(12) United States Patent
Andersson et al.

(10) Patent No.: US 7,429,354 B2
(45) Date of Patent: Sep. 30, 2008

(54) STRUCTURAL UNITS THAT DEFINE FLUIDIC FUNCTIONS

(75) Inventors: Per Andersson, Uppsala (SE); Gunnar Ekstrand, Uppsala (SE); Ulrike Selditz, Uppsala (SE); Sussanne Wallenborg, Uppsala (SE); Helene Derand, Taby (SE); Gunnar Thorsen, Uppsala (SE); Ebru Togan-Tekin, Uppsala (SE)

(73) Assignee: Gyros Patent AB, Uppsala (SE)

( * ) Notice: Subject to any disclaimer, the term of this patent is extended or adjusted under 35 U.S.C. 154(b) by 758 days.

(21) Appl. No.: 10/472,255

(22) PCT Filed: Mar. 19, 2002

(86) PCT No.: PCT/SE02/00531

§ 371 (c)(1), (2), (4) Date: Feb. 16, 2004

(87) PCT Pub. No.: WO02/074438

PCT Pub. Date: Sep. 26, 2002

(65) Prior Publication Data

US 2004/0120856 A1   Jun. 24, 2004

(30) Foreign Application Priority Data

Mar. 19, 2001 (SE) .................................. 0100951
Mar. 19, 2001 (SE) .................................. 0100952
Jan. 28, 2002 (SE) .................................. 0200242

(51) Int. Cl.
*G01N 21/00* (2006.01)
(52) U.S. Cl. ....................................................... 422/58
(58) Field of Classification Search .................... 422/58
See application file for complete search history.

(56) References Cited

U.S. PATENT DOCUMENTS 4,233,029 A    11/1980    Columbus (Continued)

FOREIGN PATENT DOCUMENTS

EP                305210           3/1989

(Continued)

OTHER PUBLICATIONS

Office Action issued Jan. 8, 2008 during the prosecution of Japanese Patent Application No. 2002-573143.

(Continued)

*Primary Examiner*—Walter D. Griffin
*Assistant Examiner*—Bobby Ramdhanie
(74) *Attorney, Agent, or Firm*—Fulbright & Jaworski, LLP

(57) ABSTRACT

A microfluidic device that comprises several microchannel structures in which there are an inlet port, an outlet port and therebetween a substructure comprising a fluidic function. The device has an axis of symmetry around which the microchannel structures are arranged as two or more concentric annular zones. for an inlet port and an outlet port of the same microchannel structure the inlet port is typically closer to the axis of symmetry than the outlet port. Each microchannel structure comprises a substructure that can retain liquid while the disc is spun around the axis and/or the inlet ports are positioned separate from the paths waste liquid leaving open waste outlet ports will follow across the surface of the disc when it is spun. For the microchannel structures of an annular zones the corresponding substructures are at essentially at the same radial distance while corresponding substructures in microchannel structures of different annular zones are at different radial distances. The invention also refers to several other substructures. The substructure are primarily adapted for transporting liquid aliquots that have a surface tnsion >5 mN/m with centrifugal force.

4 Claims, 15 Drawing Sheets

U.S. PATENT DOCUMENTS

| | | | |
|---|---|---|---|
| 4,254,083 A | 3/1981 | Columbus |
| 4,279,862 A | 7/1981 | Bretaudiere et al. |
| 4,868,129 A | 9/1989 | Gibbons et al. |
| 4,946,795 A | 8/1990 | Gibbons et al. |
| 5,230,866 A | 7/1993 | Shartle et al. |
| 5,376,252 A | 12/1994 | Ekstrom |
| 5,637,469 A | 6/1997 | Wilding et al. |
| 5,690,841 A | 11/1997 | Elderstig |
| 5,705,813 A | 1/1998 | Apffel et al. |
| 5,716,825 A | 2/1998 | Hancock et al. |
| 5,726,026 A | 3/1998 | Wilding et al. |
| 5,773,488 A | 6/1998 | Allmer |
| 5,957,167 A | 9/1999 | Feygin |
| 5,962,081 A | 10/1999 | Ohman |
| 5,995,209 A | 11/1999 | Ohman |
| 6,117,396 A | 9/2000 | Demers |
| 6,126,765 A | 10/2000 | Ohman |
| 6,130,098 A | 10/2000 | Handique et al. |
| 6,143,247 A | 11/2000 | Sheppard, Jr. et al. |
| 6,144,447 A | 11/2000 | Ohman |
| 6,192,768 B1 | 2/2001 | Wallman et al. |
| 6,203,291 B1 | 3/2001 | Stemme |
| 6,296,020 B1 | 10/2001 | McNeely et al. |
| 6,322,682 B1 | 11/2001 | Arvidsson et al. |
| 6,418,968 B1 | 7/2002 | Pezzuto et al. |
| 6,454,970 B1 | 9/2002 | Ohman |
| 6,481,453 B1 | 11/2002 | O'Connor et al. |
| 6,555,389 B1 | 4/2003 | Ullman et al. |
| 6,557,427 B2 | 5/2003 | Weigl et al. |
| 6,591,852 B1 | 7/2003 | McNeely et al. |
| 6,601,613 B2 | 8/2003 | McNeely et al. |
| 6,620,478 B1 | 9/2003 | Ohman |
| 6,632,656 B1 | 10/2003 | Thomas |
| 6,653,625 B2 | 11/2003 | Andersson et al. |
| 6,717,136 B2 | 4/2004 | Andersson |
| 6,728,644 B2 | 4/2004 | Bielik |
| 6,811,736 B1 | 11/2004 | Ohman |
| 6,812,456 B2 | 11/2004 | Andersson |
| 6,812,457 B2 | 11/2004 | Andersson |
| 2002/0003001 A1 | 1/2002 | Weigl et al. |
| 2002/0142481 A1 | 10/2002 | Andersson et al. |
| 2003/0044322 A1 | 3/2003 | Andersson |
| 2003/0047823 A1 | 3/2003 | Ohman |
| 2003/0053934 A1 | 3/2003 | Andersson |
| 2003/0054563 A1 | 3/2003 | Ljungstrom |
| 2003/0082075 A1 | 5/2003 | Agren |
| 2003/0094502 A1 | 5/2003 | Andersson et al. |
| 2003/0129360 A1 | 7/2003 | Derand |
| 2003/0156763 A1 | 8/2003 | Soderman |
| 2003/0211012 A1 | 11/2003 | Bergstrom |
| 2003/0213551 A1 | 11/2003 | Derand |
| 2003/0231312 A1 | 12/2003 | Sjoberg |
| 2004/0058408 A1 | 3/2004 | Thomas |
| 2004/0096867 A1 | 5/2004 | Andersson |
| 2004/0099310 A1 | 5/2004 | Andersson |
| 2004/0202579 A1 | 10/2004 | Larsson et al. |

FOREIGN PATENT DOCUMENTS

| | | |
|---|---|---|
| EP | 0977032 | 2/2000 |
| JP | 2001502790 | 2/2001 |
| WO | WO-9506870 | 9/1994 |
| WO | WO-9533986 | 6/1995 |
| WO | WO-9606354 | 8/1995 |
| WO | WO-9615576 | 5/1996 |
| WO | WO-9721090 | 6/1997 |
| WO | WO-9800231 | 1/1998 |
| WO | WO-9853311 | 1/1998 |
| WO | WO-9807019 | 2/1998 |
| WO | WO-9955827 | 11/1999 |
| WO | WO-9958245 | 11/1999 |
| WO | WO-0022436 | 4/2000 |
| WO | WO-0025921 | 5/2000 |
| WO | WO-0069560 | 5/2000 |
| WO | WO-0040750 | 7/2000 |
| WO | WO-0056808 | 9/2000 |
| WO | WO-0062042 | 10/2000 |
| WO | WO-0067907 | 11/2000 |
| WO | WO-0078455 | 12/2000 |
| WO | WO-0079285 | 12/2000 |
| WO | WO-0102737 | 1/2001 |
| WO | WO-0119518 | 3/2001 |
| WO | WO-0146465 | 6/2001 |
| WO | WO-0146645 | 6/2001 |
| WO | WO-0147637 | 7/2001 |
| WO | WO-0147638 | 7/2001 |
| WO | WO-0154810 | 8/2001 |
| WO | WO-0185602 | 11/2001 |
| WO | WO-0187485 | 11/2001 |
| WO | WO-0187486 | 11/2001 |
| WO | WO-0187487 | 11/2001 |
| WO | WO-0189691 | 11/2001 |
| WO | WO-0190614 | 11/2001 |
| WO | WO-0242650 | 5/2002 |
| WO | WO-03008101 | 1/2003 |

OTHER PUBLICATIONS

Tooke, Nigel High-Through Put Screening SNP Scoring in Microfabricated Device, Sep. 1999.

Ekstramd et al. "Microfluids in a Rotating CD," Micro TAS 2000, Enschede, The Netherlands, May 14-18, 2000.

Eckersten et al, "SNP Scoring in a Disposable Microfabricated CD Device," Human Genome Meeting, HGM 2000, Vancouver, Canada, Apr. 9-12, 2000.

Tooke et al, "SNP Scoring in a Disposable Microfabricated CD Device with Solid Phase Pyrosequenceing," Human Genome Meeting, HGM 2000, Vancouver, Canada, Apr. 9-12, 2000.

Gustafsson et al, "Integrated Sample Preparation and Detection on a Microfluidic Compact Disk (CD) Decreases Detection Limits for Protein Identification by Mass Spectrometry," Proceedings of the 49th ASMS Conference on Mass Spectometry and Allied Topics, Chicago, Illinois, May 27-31, 2001.

Dong et al, J. Coll. Interface Science 172 (1995), pp. 278-288.

Handique et al., SPIE Proceedings 3224 (1997) 185-195.

U.S. Appl. No. 09/674,457, Larsson et al.
U.S. Appl. No. 09/830,475, Stjernstrom.
U.S. Appl. No. 09/937,533, Larsson et al.
U.S. Appl. No. 09/958,577, Ulfendahl.
U.S. Appl. No. 10/030,297, Derand et al.
U.S. Appl. No. 10/129,032, Tormod.
U.S. Appl. No. 10/111,822, Tooke et al.
U.S. Appl. No. 10/069,827, Derand et al.
U.S. Appl. No. 10/182,792, Derand et al.
U.S. Appl. No. 10/168,942, Tooke et al.
U.S. Appl. No. 10/169,056, Andersson et al.
U.S. Appl. No. 10/402,138, Kylberg et al.
U.S. Appl. No. 10/402,137, Kylberg et al.
U.S. Appl. No. 10/450,177, Ohman et al.
U.S. Appl. No. 10/276,282, Larsson et al.
U.S. Appl. No. 10/070,912, Ohman et al.
U.S. Appl. No. 10/244,667, Agren.
U.S. Appl. No. 10/957,452, Ekstrand et al.
U.S. Appl. No. 10/849,321, Fielden et al.
U.S. Appl. No. 10/867,893, Derand et al.
U.S. Appl. No. 10/999,532, Ostlin et al.
U.S. Appl. No. 09/937,533, Derand et al.
U.S. Appl. No. 10/513,084, Holmquest et al.
U.S. Appl. No. 10/924,151, Tooke et al.
U.S. Appl. No. 09/869,554, Orlefors et al.

Fig. 1
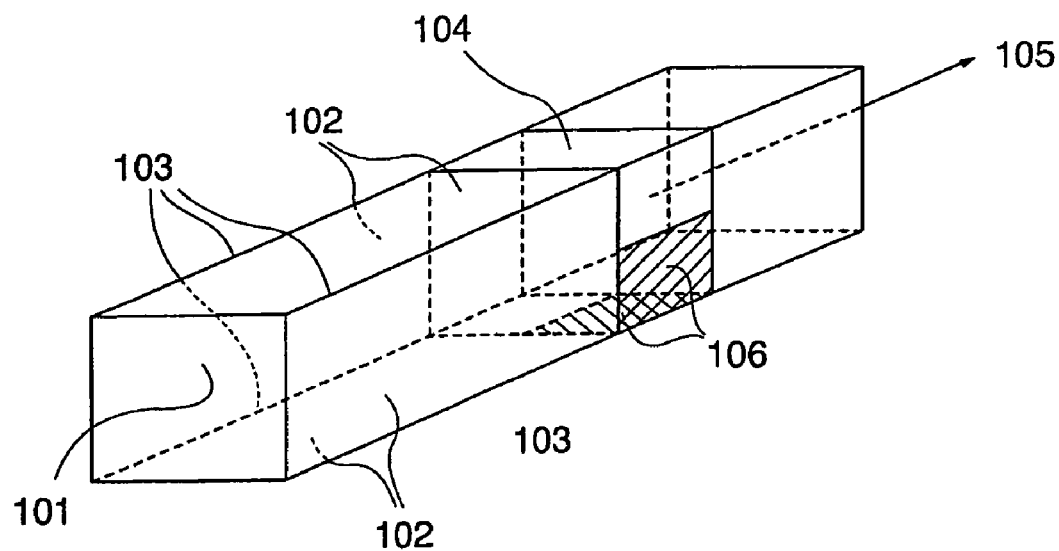
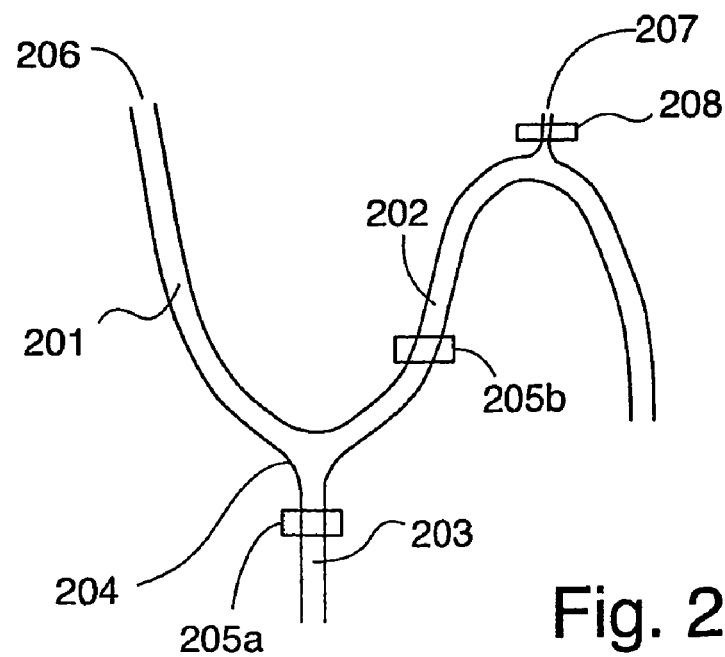
Fig. 2

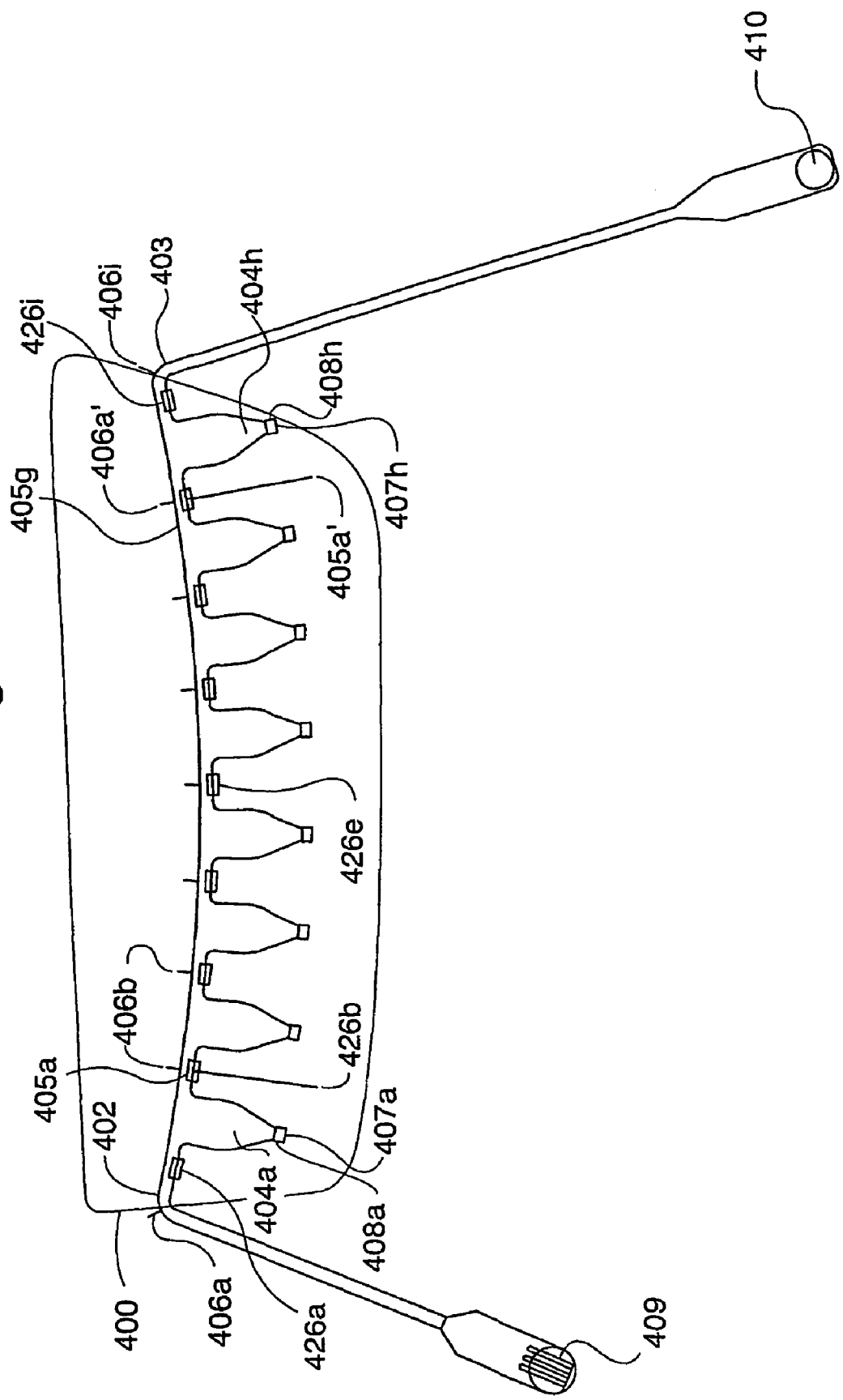

STRUCTURAL UNITS THAT DEFINE FLUIDIC FUNCTIONS

TECHNICAL FIELD

The present invention concerns a microfluidic device in which there is a microchannel structure which comprises (a) one or more inlet ports, (b) one or more outlet ports, and (c) a structural unit which comprises a fluidic function and is located between one of the inlet ports and one of the outlet ports. The term "outlet port" includes-that the port is an outlet for liquid and/or an inlet and/or an outlet vent to ambient atmosphere. The structural unit (c) may include an inlet or an outlet port. There may be two or more structural units having the same or different fluidic function between an inlet port and an outlet port.

The microchannel structure of the present invention is intended for transport and processing of one or more liquid aliquots. The aliquots may have the same or different compositions.

The invention also concerns various methods in which the microfluidic device is used.

DRAWINGS

The structural units (functional units) are illustrated in FIGS. 2-13. The view is from above. The cross-sectional areas are typical rectangular.

FIG. 1 illustrates the definitions of "edge" and "circumferential zone".

FIG. 2 illustrates a functional unit that enables split flow (unit 1).

Figure 3A:
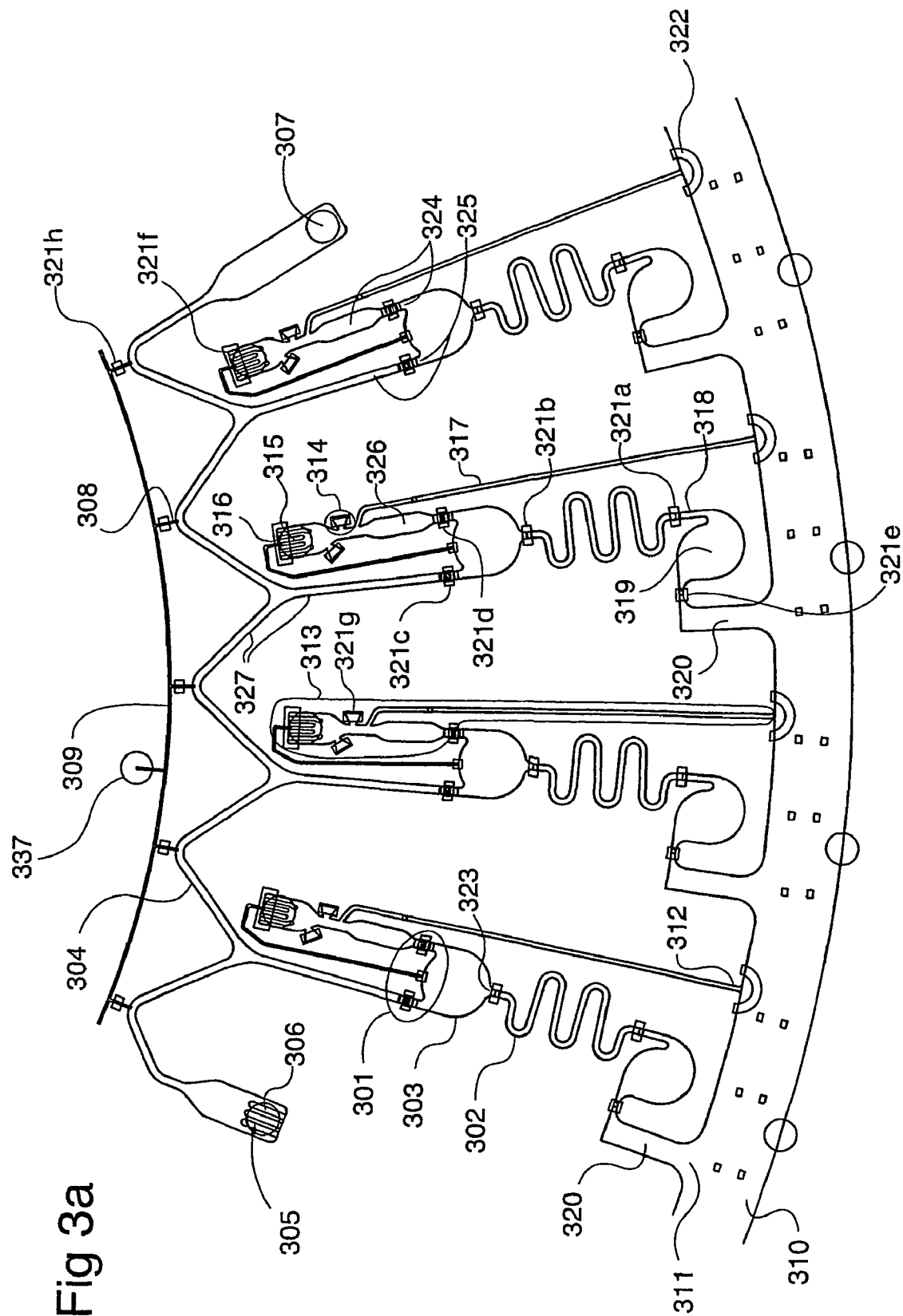
Figure 3B:
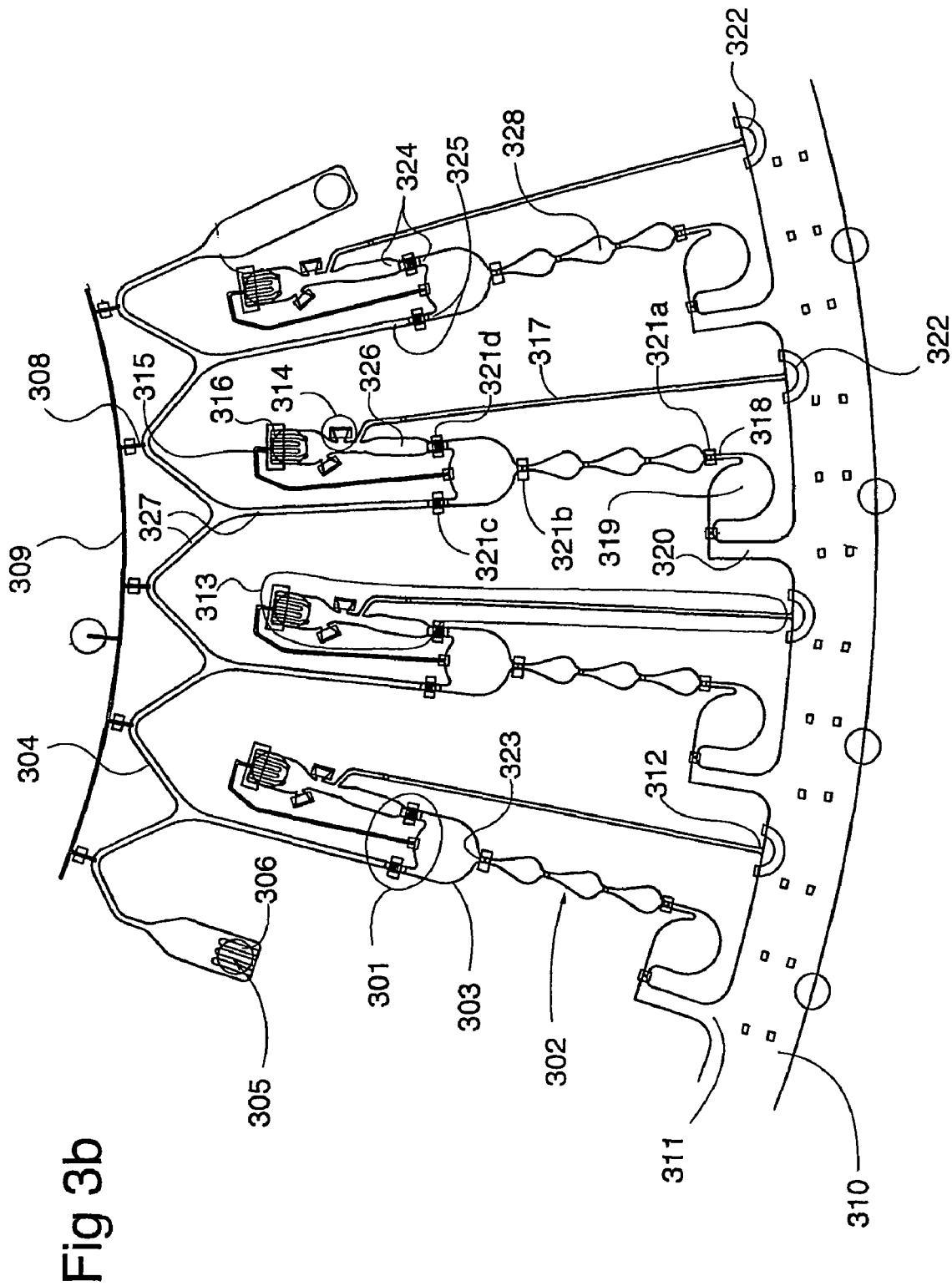
Figure 3C:
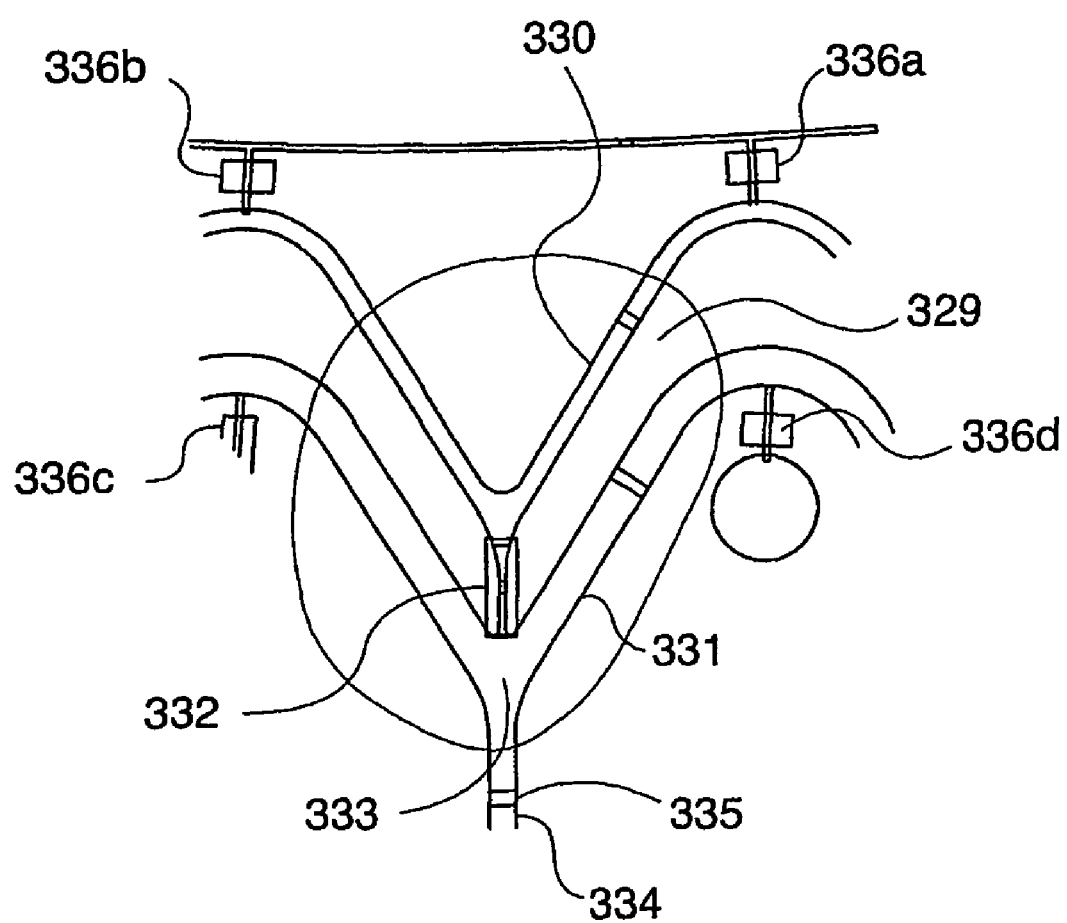

FIGS. 3a-c illustrate a functional unit that enables mixing (unit 2).

Figure 4A:
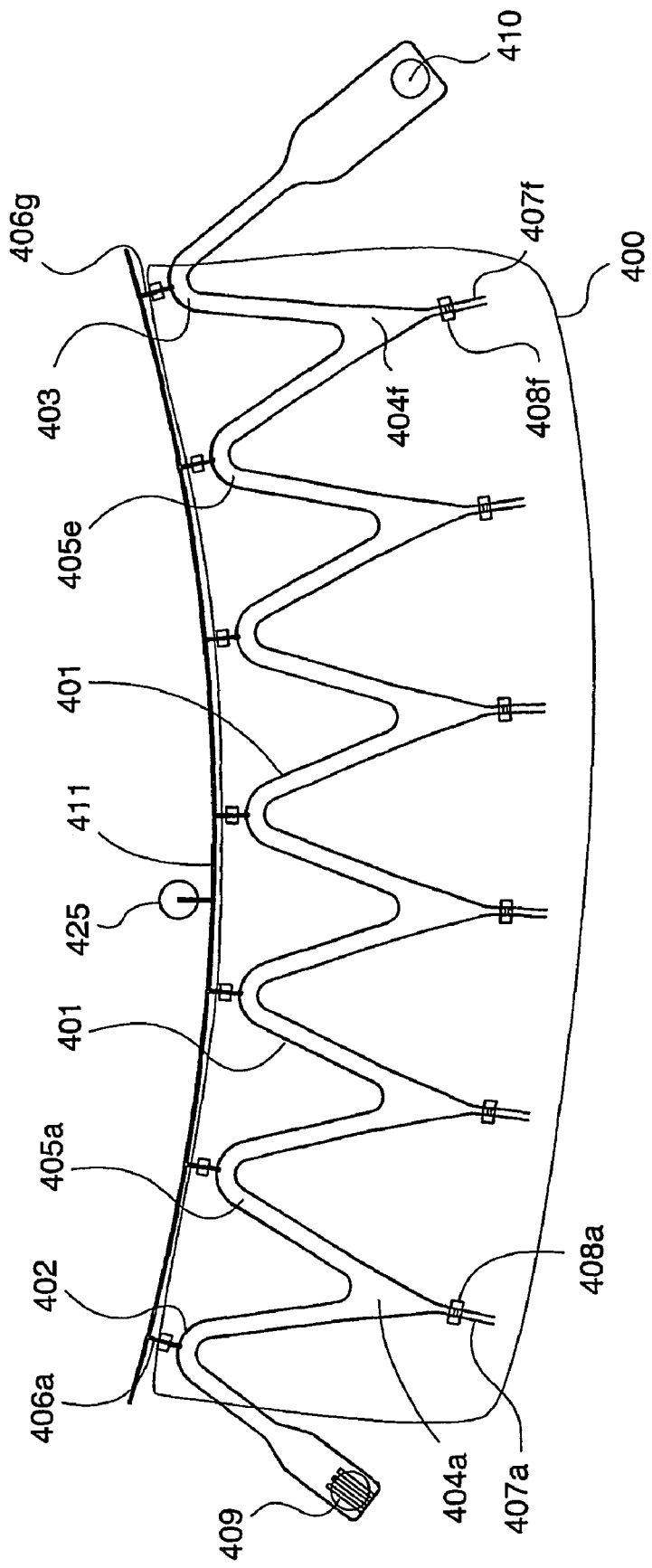
Figure 4C:
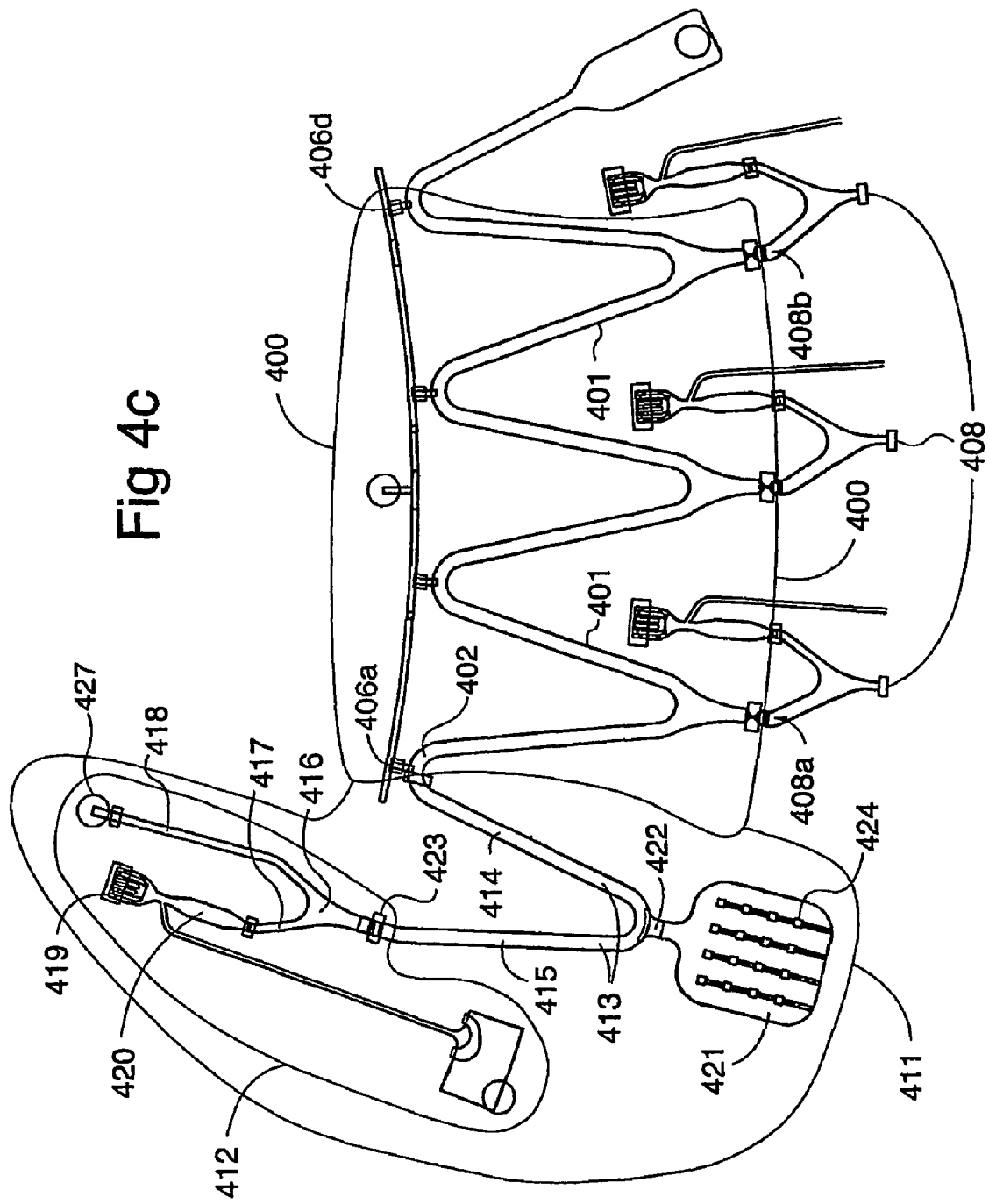

FIGS. 4a-c illustrate a functional unit that enables partition of a larger liquid aliquot to smaller aliquots and distribution of these into different microchannel structures (unit 3).

Figure 5:
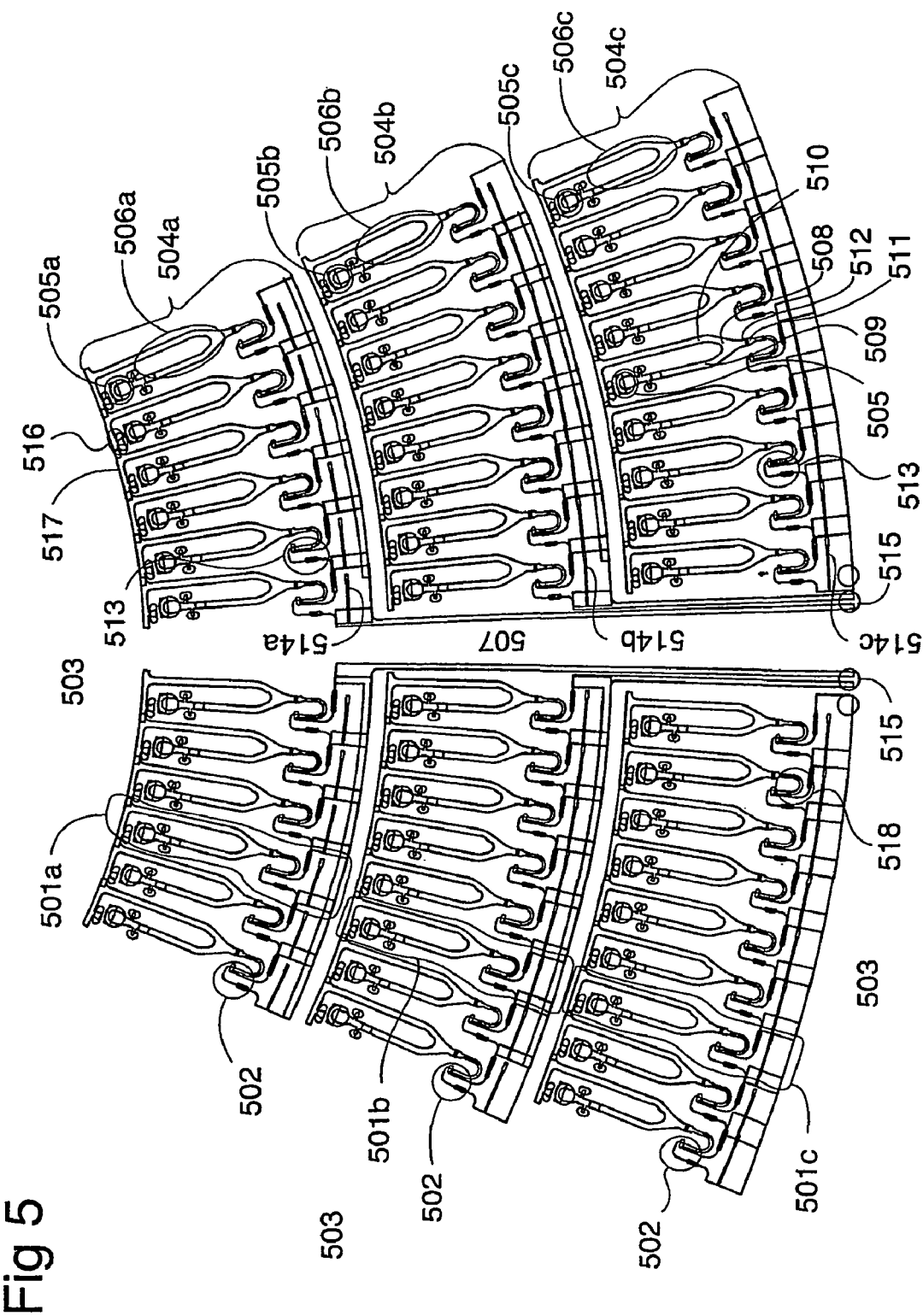

FIG. 5 illustrates a plurality of microchannel structures that has been arranged in subgroups in the form of three annular rings/zones on a planar substrate and functional units that are preferred for this kind of arrangement (unit 4).

Figure 6C:
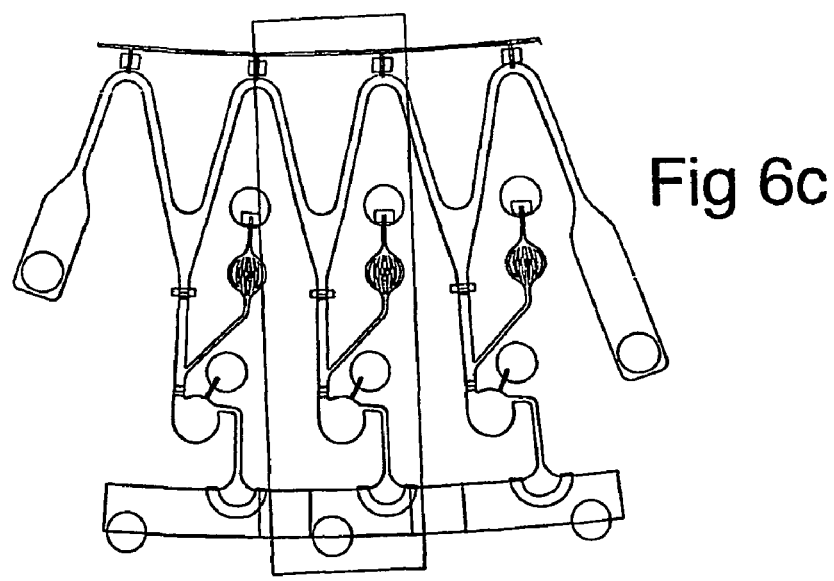
Figure 6B:
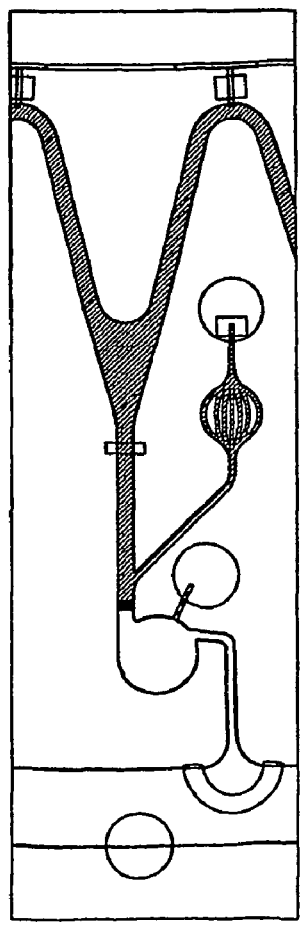
Figure 6A:
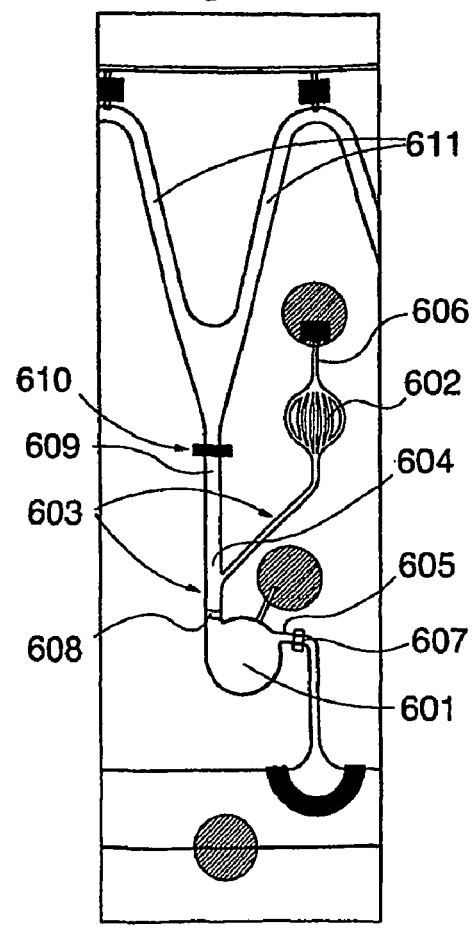

FIGS. 6a-c illustrate a functional unit that enables transport back and forth of a liquid aliquot within a microchannel structure (unit 5).

Figure 7A:
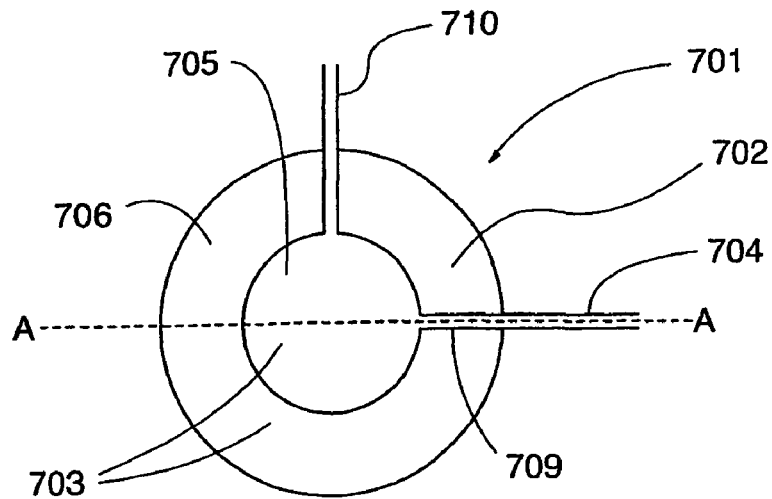
Figure 7B:
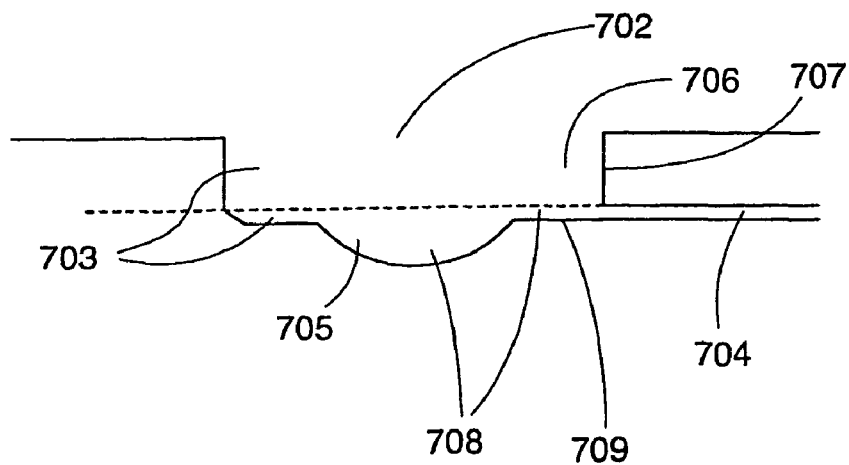
Figure 7C:
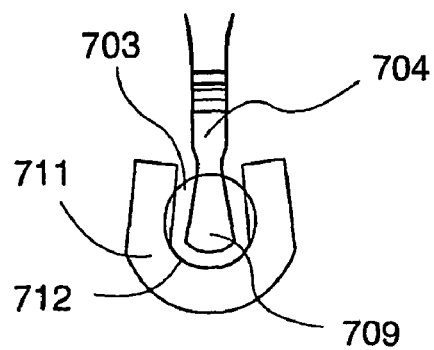

FIGS. 7a-c illustrate a functional unit that enables controlled evaporation (unit 6).

Figure 8A:
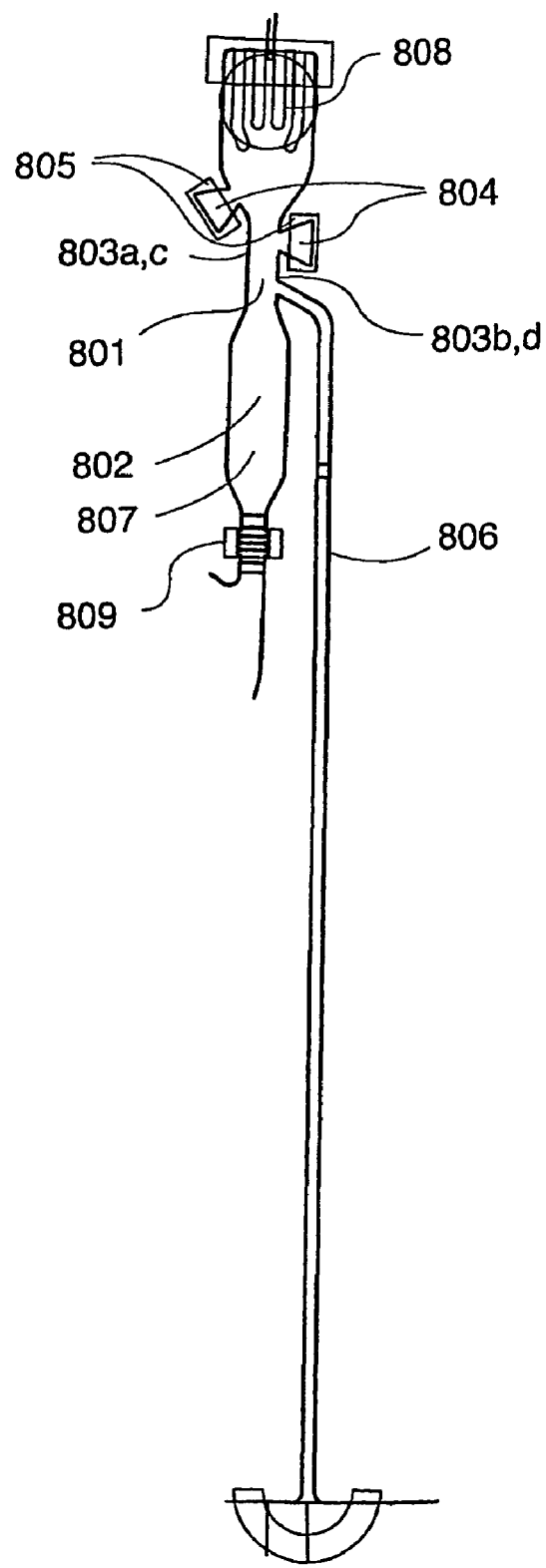
Figure 8B:
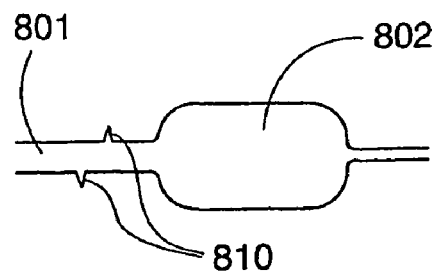
Figure 8C:
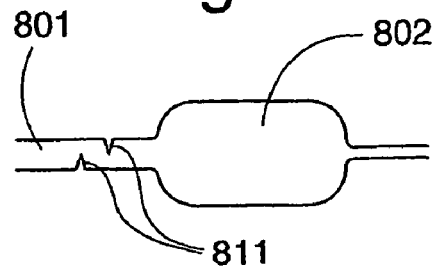

FIGS. 8a-8c illustrate a functional unit that comprises antiwicking means (unit 7).

FIG. 9 illustrates a functional unit in which it is possible to create a liquid flow that has front zone with a different composition compared to the bulk flow (unit 8).

Figure 10:
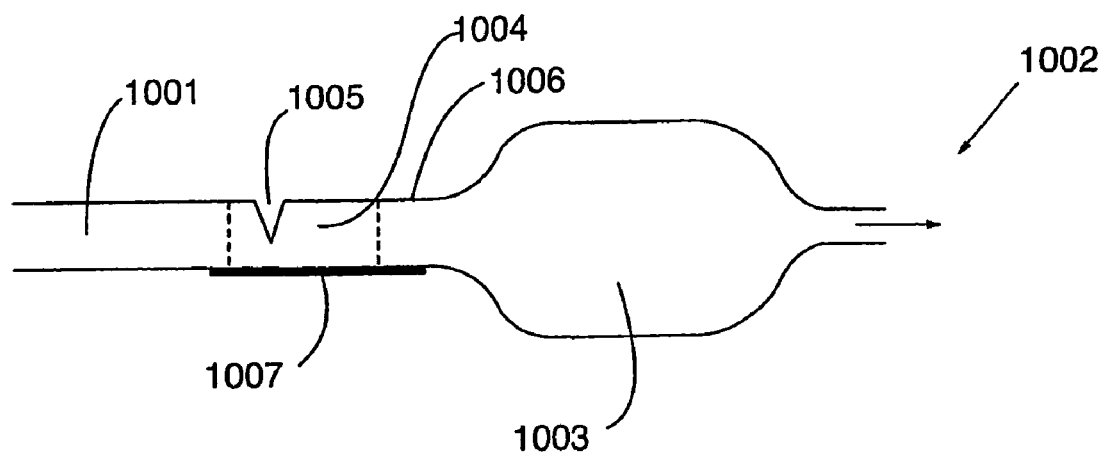

FIG. 10 illustrates a functional unit that comprises a non-closing inner valve (unit 9).

Figure 11A:
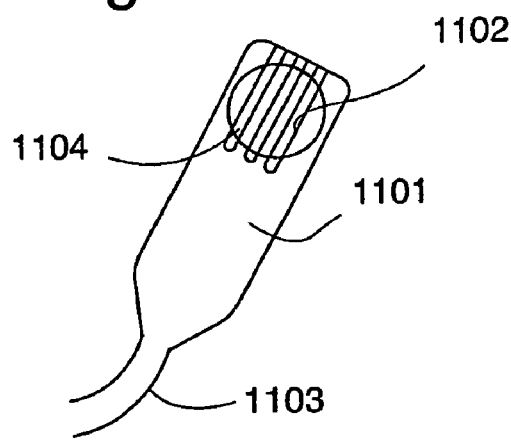

FIGS. 11a & b illustrate a functional unit that facilitates liquid penetration from an inlet port (unit 10).

Figure 12:
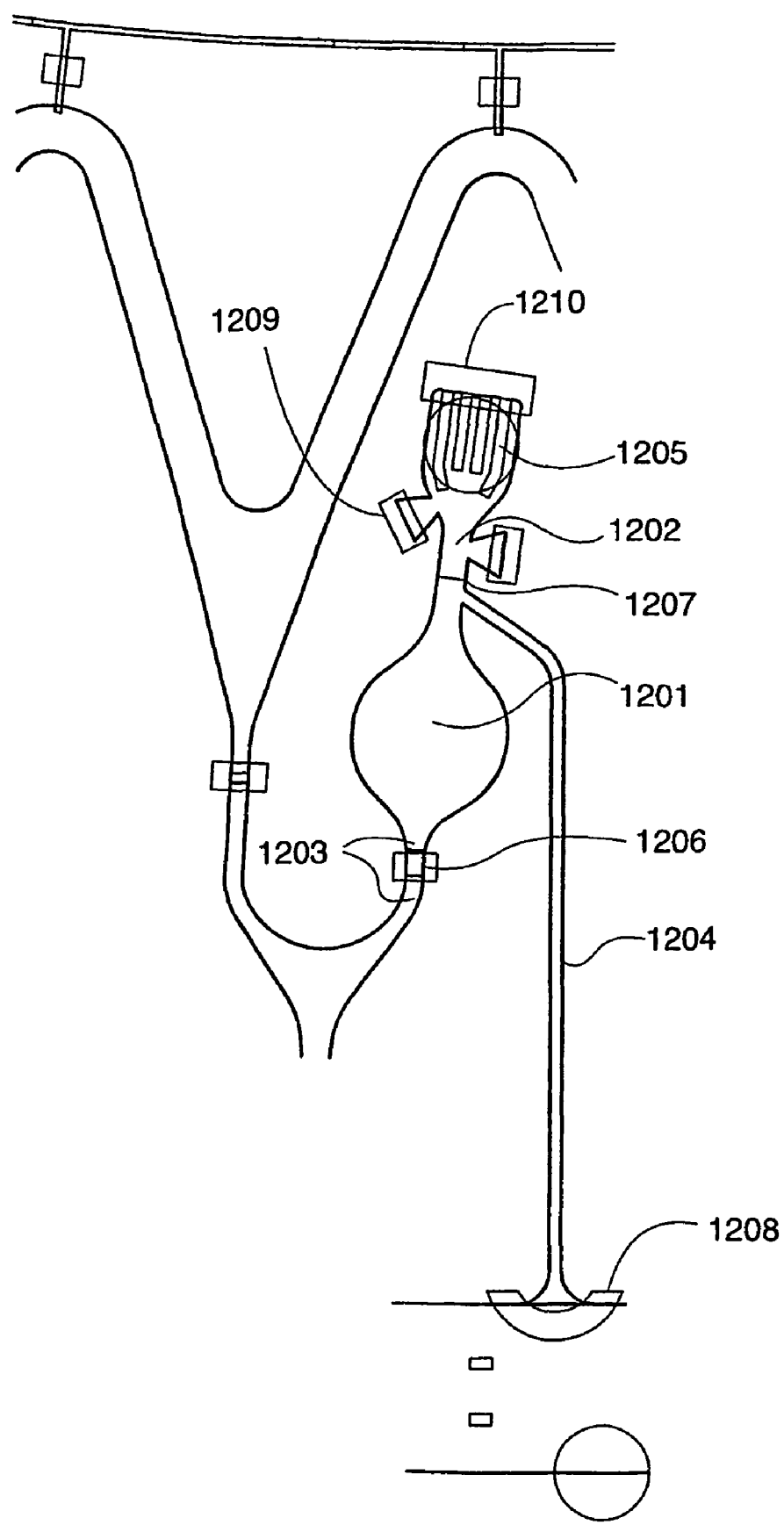

FIG. 12 illustrates a functional unit that comprises a volume-defining structure that can be integrated in a microchannel structure (unit 11).

Figure 13B:
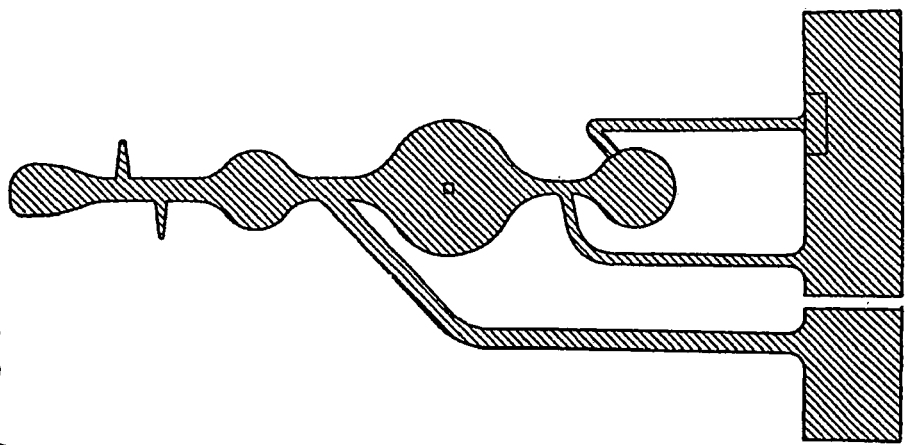
Figure 13A:
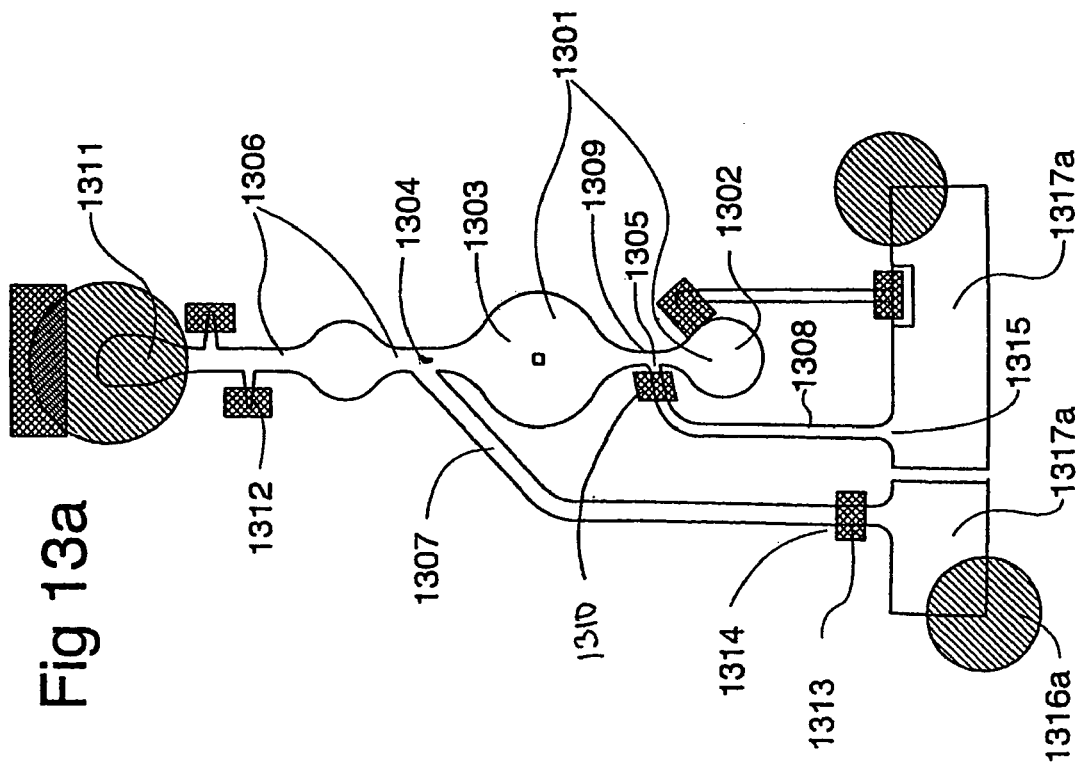

FIGS. 13a & b illustrate a functional unit that enables physical separation of particulate material from a liquid (unit 12).

GENERAL DEFINITIONS

The terms "microformat", "microchannel" etc contemplate that a microchannel structure comprises one or more cavities and/or channels that have a depth and/or a width that is $\leq 10^3$ µm, preferably $\leq 10^2$ µm. The lower limit for the width/breadth is typically significantly larger than the size of the largest reagents and constituents of aliquots that are to pass through a microchannel. The volumes of microcavities/microchambers are typically $\leq 1000$ nl, such as $\leq 500$ nl or $\leq 100$ nl or $\leq 50$ nl (nano-litre range). Chambers/cavities directly connected to inlet ports may be considerably larger, e.g. microchambers/microcavities intended for application of sample and/or washing liquids. Typical volumes in these latter cases are within intervals such as 1-10 µl, 1-100 µl, 1-1000 µl (micro-litre range) or even broader intervals.

The present invention is primarily intended for geometric arrangements in which the microchannel structure is present in a substrate having an axis of symmetry (spinning axis). The term "radial distance" means the shortest distance between an object and the axis of symmetry. A microchannel structure has an inlet port which is upstream a structural unit. The radial distance for an inlet port and a structural unit may be the same, or the inlet port may be at a shorter or longer radial distance compared to the structural unit. In a typical case there is also an outlet port for liquid downstream the structural unit, which in most cases is at a larger radial distance than the inlet port. The microchannel structure may or may not be oriented in a plane perpendicular to the axis of symmetry. By spinning the substrate around its axis of symmetry (spinning axis), a liquid aliquot positioned at a particular radial position, for instance in a particular structural unit, will be subjected to a centrifugal force tending to drive the liquid outwards towards the periphery of the disc. In this way a liquid aliquot may be transported from an inlet port to an outlet port via a functional unit if the microchannel structure is designed to permit this. In this kind of systems a "higher" or an "upper" level/position will be at a shorter radial distance (inner position) compared to a "lower" level/position (outer position). Similarly, the terms "up", "upward", "inwards", and "down", "downwards", "outwards" etc will mean towards and from, respectively, the spinning axis. This terminology applies if not otherwise is specified.

With respect to other arrangement/substrates and conventional driving forces, i.e. gravity force, externally applied pressure, electro-osmotically (electrokinetically. electroendoosmosis etc) driven flows etc, these terms have their conventional meaning.

The terms "downstream" and "upstream" are related to the process protocols and liquid flow as such. The terms thus refer to the order in which a unit, a part, a process step, etc is utilized. A downstream position is coming after an upstream position.

Axes of symmetry are n-numbered ($C_n$) where n is an integer between 2 and $\infty$, preferably 6, 7, 8 and larger, for instance $\infty$. In preferred cases the substrate as such has a cylindrical, spherical or conical symmetry ($C_\infty$).

A preferred substrate is in the form of a disk.

Each microchannel structure of the invention contains the functional units necessary to carry out a predetermined protocol within the structure. Parts that are common for several microchannel structures, such as common distribution channels, common waste channels, common inlet ports, common outlet ports etc, are considered to be part of each microchannel structure to which they are connected.

The term microconduit means a part of a microchannel structure.

If not otherwise indicated the term "edge" of a microchannel/microconduit will refer to the intersection of two inner walls of a microchannel. This kind of edges is typically more or less length-going in the flow-direction. See FIG. 1 which shows a microchannel having a rectangular cross-section (101), four inner walls (102) with four wall intersections or edges (103). The arrow (105) gives the flow direction.

A circumferential zone of a microchannel is also illustrated in FIG. 1. It is a surface zone (104) in the inner wall of a microchannel and extends in a sleeve-like manner fully around the flow direction (105). The length of this kind of zone is at least from 0.1 to 10, 100, 1000 or more times the breadth or depth of the microchannel/microconduit at the upstream end of the zone. A "segment" (106) of a circumferential zone is a part that stretches across the zone in the flow direction (flow-directed segment). A segment may extend into one, two, three or four of the inner walls of the microchannel.

The term "surface characteristics" refers to the surface of an inner wall of a microchannel. In the context of the invention the term contemplates mainly two subgroups:
(i) geometric surface characteristics, for instance presence of projections/protrusions from and depressions in the inner wall, and
(ii) chemical surface characteristics.

Wettability of a surface depends on surface characteristics and on properties of the liquid aliquot in contact with the surface. Wettability is often measured as the liquid contact angle. By the term "wettable" is mostly contemplated that the liquid contact angle is $\leq 90°$, such as $\leq 70°$ or $\leq 40°$. By the term "non-wettable" is mostly contemplated that the liquid contact angle is $\geq 90°$. The term non-wettable may sometimes refer to liquid contact angles that are less than 90°, e.g. $\geq 40°$ such as $\geq 70°$, however, it then mostly refer to a bordering area that has a lower liquid contact angle. The liquid contact angle in the normal case refers to equilibrium contact angles although it sometimes may refer to receding and/or advancing contact angles depending on the purpose of a measurement. In the context of the invention equilibrium contact angles are primarily contemplated. The figures given refer to values at the temperature of use. Non-wettable surfaces are often called hydrophobic, in particular in relation to aqueous media.

The term "inner valves" refers to valves in which the passage or non-passage depends on physico-chemical properties of the liquid and the material in the inner wall surface of a microconduit and/or the curvature of the microconduit in the valve.

The term "non-closing valves" refers to valves in which a liquid is stopped at the valve even if the microconduit at the valve position is opened. This kind of valves may also be called passive valves.

The term "closing valves" refers to valves in which a valve part is used to physically close a microconduit.

The term "geometric valves" means that the valving function is obtained by a specific curvature possibly combined with a branching of a microconduit/microchannel.

The term "surface break" refers to a change in chemical surface characteristics. The change may be local and present in a circumferential zone or in a segment of such a zone. In the context of the present invention the term typically means a decrease in wettability of an inner surface in a microchannel/microconduit when moving in the downstream direction.

Background Technology

Microfluidic structures have been considered promising for assays, chemical synthesis etc which are to be performed with a high degree of parallelity. A generally expressed desire has been to run the complete sequence of steps of test protocols, including sample treatment within microfluidic devices. This has lead to a desire to dense-pack microchannel structures on planar substrates (chips) and to integrate valve functions, separation functions, means for moving liquids etc within microfluidic devices. In the macroscopic world these kinds of functionalities can easily be integrated into various kinds of liquid transportation systems, but in the microscopic world it has become expensive, unreliable etc to miniaturize the macroscopic designs. There has thus been a desire to redesign the functionalities. The situation becomes still worse when moving from μl- to nl-aliquots or from microchannel dimensions of above 100 μm down to those less than 100 μm.

Background Publications

The background publications refer to variants that may be applied to various subaspects of the present invention. These publications will be discussed under the heading "The invention".

Patent applications and issued patents are hereby incorporated by reference.

Objectives

Major objective: The present invention provides novel fluidic functionalities that can be used when transporting and processing nl-volumes of liquids in microchannel systems of the kind defined under the heading "Technical Field". A particular intention is to create functionalities that do not require movable mechanical parts, e.g. to accomplish valving, pumping, mixing etc, and can be integrated into the microchannels and/or the substrates. The various novel functionalities are based on local surface characteristics of the inner walls of the microchannels and/or on properties of the liquids, such as surface tension and wetting ability.

Other Objectives

A first objective is to provide a simplified microfluid functionality that enables directing selectively a first liquid aliquot from an incoming microconduit into a first branch and a subsequent liquid aliquot into a second branch.

A second objective is to provide a microfluid functionality that is simple and permits quick, safe and reliable mixing of two liquid aliquots that are miscible with each other.

A third objective is to provide a microfluid functionality for distributing liquid aliquots in parallel to separate substructures of a plurality of microchannel structures.

A fourth objective is to provide microfluid functionalities that facilitate
(a) arranging a plurality of microchannel structures in two or more annular zones in
   a substrate having an axis of symmetry, and
(b) utilizing centrifugal force for transporting liquids within the individual microchannel structures.

A fifth objective is to provide a microfluid functionality in which a liquid aliquot can be transported back and forth between two microcavities.

A sixth objective is to provide a microfluid functionality that enables quick and controlled evaporation of a liquid from a microchannel structure.

A seventh objective is to provide a microfluid functionality that is anti-wicking.

An eighth objective is to provide a microfluid functionality that can be used for creating a prezone of a first liquid in front of a second main liquid (bulk aliquot). This functionality may be useful when dispensing a liquid aliquot under the protection of another liquid and/or when improving liquid penetration into a microchamber/microcavities.

A ninth objective is to provide an alternative inner valve for microfluidic systems.

A tenth objective is to provide a microfluid functionality facilitating rapid introduction of a liquid aliquot into a microchannel structure.

An eleventh objective is to provide a microfluid functionality which enables reproducibly metering of a liquid aliquot within a microchannel structure before the aliquot is transported farther downstream.

A twelfth objective is to provide a liquid functionality facilitating separation of particulate material from a liquid aliquot within a microchannel structure.

The Invention

We have now found that these objectives can be at least partially met in a microfluidic device as defined in the first paragraph under the heading "Technical Field".

In one of its broadest aspect, the invention is among others based on the recognition that the appropriate surface tension of a liquid is important for controlling a liquid flow in a microsystem. This in particular applies when dealing with liquid aliquots in the nano-litre range and/or if the control is exerted without mechanical valves and pumps, i.e. by driving the transport of liquid aliquots through a functional unit of the invention by capillary force and/or inertia force etc. Typical examples of inertia force are gravitational force and centrifugal force.

Summary of the First Main Aspect of the Invention.

In a first main aspect, the invention is a method for transporting one, two or more liquid aliquots through a microchannel structure of the microfluidic device, which is generally defined under the heading "Technical Field". The method comprises the steps of (i) providing the microfluidic device,
(ii) providing said one, two or more liquid aliquots,
(iii) introducing each of said aliquots through an inlet port of one, two or more microchannel structures of the device,
(iv) transporting the aliquots through at least one of the structural units which is present between an inlet port and an outlet port without utilizing valves and pumps containing movable mechanical parts, and
(v) possibly collecting the aliquots in treated form in one or more of the outlet ports of the microchannel structure.

This first aspect is characterized in that one, two, three or more of the liquid aliquots that are to be introduced through an inlet port of the microchannel structures have a surface tension which is $\geq 5$ mN/m, such as $\geq 10$ mN/m or $\geq 20$ mN/m.

The microfluidic device provided in step (i) comprises in the preferred variants a structural unit that may be of the kind discussed below for the various subaspects of the microfluidic device of the invention, for instance structural units 1-12 including units that may combine the functionalities and/or structures of two or more of the units 1-12.

In step (ii), at least one of the liquid aliquots has a volume in the nano-litre range.

In step (iii) two or more of the aliquots may be introduced via the same or different inlet ports.

In step (iv) the driving force utilized for transport of the aliquots typically is capillary force and/or inertia force without excluding other kinds of forces as discussed elsewhere in this specification.

In step (v) the term "treated form" contemplates that the aliquots have passed the structure and been subjected to one or more predetermined treatments. This means that the chemical composition may have changed and/or that aliquots may have been mixed during passage of the microchannel structure. Typical treatments include bioaffinity reactions, chemical reactions, depletion of one or more predetermined components of a starting aliquot, buffer exchange, concentrating, mixing of aliquots etc.

At least one of the aliquots is typically aqueous and/or may contain one or more surface-active agents that increase or decrease the surface-tension of a liquid, such as water. Typical agents that reduce surface tension are detergents that may be cationic, anionic, amphoteric or non-ionisable. Surface-active agents also include organic solvents, preferably miscible with water. Examples are methanol, ethanol, isopropanol, formamide, acetonitrile etc. Charged or chargeable polymers, biomolecules such as proteins, certain sugars etc may also act as surface-active agents.

The volumes of the liquid aliquots which are to be transported according to the invention are typically in the nanoliter range, i.e. $\leq 1000$ nl, such as $\leq 500$ nl or $\leq 100$ nl or $\leq 50$ nl. These small volumes primarily refer to sample and/or reagent volumes and do not exclude that other volumes may be used in combination with a volume in the nanoliter range.

The volume and composition of the different aliquots transported through a microchannel structure of the invention may be identical or different.

Summary of the Second Main Aspect of the Invention

In a second main aspect, the invention relates to the microfluidic device as generally defined in the first paragraph under the heading "Technical Field". The main characteristic of this aspect of the invention is that at least one of the structural units that are positioned downstream an inlet port is selected amongst units 1-12 as described below. Units that combine the functionality and/or structure of two or more of the units 1-12 may be included. In preferred variants of this aspect at least one of the aliquots referred to in the description of a structural unit should have a surface tension, which is $\geq 5$ mN/m, such as $\geq 10$ mN/m or $\geq 20$ mN/m.

In both of the two main aspects of the invention a microchannel structure may also comprise alternatives to units 1-12 and their combinations as long as at least one unit 1-12 is present. Alternative units are in many cases known in the field. See the background publications discussed below. The microchannel structures may also comprise hitherto unknown units.

Microchannel Structures, their Subunits and Arrangement on a Substrate Including References to Background Publications.

A microchannel structure may comprise a number of functional units, such as one or more units selected amongst inlet ports, outlet ports, units for distributing samples, liquids and/or reagents to individual microchannel structures, microconduits for liquid transport, units for defining liquid volumes, valving units, units venting to ambient atmosphere, units for mixing liquids, units for performing chemical reactions or bioreactions, units for separating soluble constituents or particulate materials from a liquid phase, waste liquid units including waste cavities and overflow channels, detection units, units for collecting a liquid aliquot processed in the structure and to be transferred to another device e.g. for analysis, branching units for merging or dividing a liquid flow, etc. In one and the same microchannel structure there may be several inlet ports and/or several outlet ports that are located at the same or different levels and connected to the main flow path via microchannel parts at a different or at the same downstream position. These microchannel parts may also contain functional units as discussed above.

The microfluidic device of the present invention typically comprises one, two, three, four or more sets of microchannel structures. Typically there are in total $\geq 50$, such as $\geq 100$ or $\geq 200$, microchannel structures per microfluidic device. The microchannel structures of a set are essentially identical and may or may not extend in a common plane of a substrate. There may be channels providing liquid communication between individual microchannel structures of a set and/or to one or more other sets that may be present in the same substrate. The microchannels are typically covered, i.e. surrounded by walls or other means for directing the flow and to lower evaporation. Openings such as in inlet ports, outlet ports, vents etc are typically present where appropriate.

The cross-section of a microchannel may have rounded forms all around, i.e. be circular, ellipsoid etc. A microchannel may also have inner edges, i.e. have cross-sections that are triangular, squaric, rectangular, partly rounded, planar etc. A part of a microchannel structure may define a space in which a liquid aliquot is treated. This kind of parts are typically called microcavities or microchambers irrespective of their dimensions in relation to surrounding parts of the microchannel structure, i.e. they may have the same or a different geometry compared to surrounding microchannel parts.

A microchannel structure may be arranged with an inlet port at an inner position and a downstream structural unit at an outer position in a substrate having an axis of symmetry. In this kind of substrates the microchannel structures may define an annular zone/ring. The breadth of the zone is equal to the difference in radial distance for the outermost and innermost part of the microchannel structures. The microchannel structures may be distributed evenly over the zone or only in one or more of its sectors. The center of the zone/ring may or may not coincide with the axis of symmetry. Different annular zones may be partly over-lapping.

Circular discs as substrates containing radially oriented microchannel structures have been described in a number of patent applications. See for instance A number of publications referring to the use of centrifugal force for moving liquids within microfluidic systems have appeared during the last years. See for instance WO 9721090 (Gamera Bioscience), WO 9807019 (Gamera Bioscience) WO 9853311 (Gamera Bioscience), WO 9955827 (Gyros AB), WO 9958245 (Gyros AB), WO 0025921 (Gyros AB), WO 0040750 (Gyros AB), WO 0056808 (Gyros AB), WO 0062042 (Gyros AB), WO 0102737 (Gyros AB), WO 0146465 (Gyros AB), WO 0147637, (Gyros AB), WO 0154810 (Gyros AB), WO 0147638 (Gyros AB), See also presentations made by Gyros AB at various scientific meetings:
(1) High-through put screening SNP scoring in microfabricated device. Nigel Tooke (September 1999);
(2) Microfluidics in a rotating CD (Ekstrand et al) MicroTAS 2000, Enschede, The Netherlands, May 14-18, 2000.
(3) (a) SNP scoring in a disposable microfabricated CD device (Eckersten et al) and (b) SNP scoring in a disposable microfabricated CD device combined with solid phase Pyrosequencing™ (Tooke et al) Human Genome Meeting, HGM 2000, Vancouver, Canada, Apr. 9-12, 2000, Integrated sample preparation and MALDI MS on a microfluidic compact disc (CD with improved sensitivity (Magnus Gustavsson et al) ASMS 2001 (spring 2001).

The microfluidic device is typically in the form of a disc. The devices can be manufactured from inorganic or organic material. Typical inorganic materials are silicon, quartz, glass etc. Typical organic materials are plastics including elastomers, such as rubber silicone polymers (for instance poly dimethyl silicone) etc. Typically, open microstructures are formed in the surface of a planar substrate by various techniques such as etching, laser ablation, lithography, replication etc. Each substrate material typically has its preferred techniques. The microstructures are designed such that when the surfaces of two planar substratres are apposed the desired enclosed microchannel structure is formed between the two substrates. From the manufacturing point of view, plastic material are preferred and the microstructures, typically in the form of open microchannels are formed by replication, such as embossing, moulding, casting etc. The open microchannel structures are then covered by a top substrate. See for instance WO 9116966 (Pharmacia Biotech AB). At the priority date of this invention the preferred plastic material was polycarbonates and plastic material based on monomers which consist of a polymerisable carbon-carbon double or triple bonds and saturated branched straight or cyclic alkyl and/or alkylene groups. Typical examples are Zeonex™ and Zeonor™ from Nippon Zeon, Japan, with preference for the latter. See for instance WO 0056808 (Gyros AB). In the preferred variants the surfaces of the open microchannel structures are typically hydrophilised, for instance as described in WO 0056808 (Gyros AB) and covered by a lid, for instance by thermolaminating as described in WO 0154810 (Gyros AB). If necessary the inner surfaces is subsequently coated with a non-ionic hydrophilic polymer as described in WO 0056808 (Gyros AB). The preferred variants are the same as given in these publications. Where appropriate hydrophobic surface breaks are introduced as outlined in WO 9958245 (Gyros AB). See also WO 0185602 (Åmic AB & Gyros AB)

The discs are preferably of the same dimension as a conventional CD, but may also be smaller, for instance down to 10% of conventional CDs, or larger, for instance up more than 200% or more than 400% of a conventional CD. These percentage values refer to the radius.

The exact demand on liquid contact angles of inner surfaces of the microchannel structure may vary between different functional units. Except for local hydrophobic surface breaks the liquid contact angel for at least two or three inner walls of a microconduit at a particular location should be wettable for the liquid to be transported, with preference for liquid contact angels that are $\leq 60°$, such as $\leq 50°$ or $\leq 40°$ or $\leq 30°$ or $\leq 20°$. In the case one or more walls have higher liquid contact angles, for instance by being non-wettable, this can be compensated by a lowered liquid contact angle on the remaining walls. This may be particular important if non-wettable lids are used to cover open microchannel structures. The values above apply to the liquid to be transported, to the functional units given above (except for local hydrophobic surface breaks) and at the temperature of use. Surfaces having water contact angles within the limits given above may often be used for other aqueous liquids.

Valve Functions.

Three categories of valves that previously have been suggested for microfluidic devices are:
1. Mechanical valves which are based on movable mechanical parts in the microchannel at the position of the valve function,
2. Valves that comprise intersecting channels and means that determine through which channel a liquid flow shall be created. A typical example is electrokinetic flow in two or more intersecting channels and switching the electrodes in order to regulate through which channels the flow shall be guided.
3. Inner valves as defined above.

Type 1 valves typically require physically closing a microconduit and are therefore "closing".

Type 2 valves function without closing a microchannel and are therefore "non-closing". They are illustrated in U.S. Pat. No. 5,716,825 Hewlett Packard) and U.S. Pat. No. 5,705,813 (Hewlett Packard).

For type 3 valves non-passage or passage of a liquid may be based on:
(a) a change in the cross-sectional area in a microconduit at the valve position by changing the energy input to the material (closing valves), and/or
(b) a local increase in the interaction energy between a through-flowing liquid aliquot and an inner surface of a microconduit at the valve position (non-closing valves), and/or
(c) a suitable curvature of the microconduit at the valve function (geometric valves).

Type 3a valves are illustrated by valves in which a physical closure is removed or created by applying energy to the material in the wall of the microconduit at the valve position. See WO 0102737 (Gyros AB) in which hindrance is accomplished by a stimulus-responsive polymer (intelligent polymer) within a part of a microchannel, and WO 9721090 (Gamera) in which hindrance is suggested by relaxation of non-equilibrium polymeric structures placed at the position of the valve. WO 97210190 (Gamera) also suggests valves that are based meltable wax plugs.

In type 3b valves the microchannel at the position of the valve is open even if the liquid is stopped (inner valves including capillary valves, also called passive valves). Through flow in this kind of valves is accomplished simply by increasing the force driving the liquid. This kind of valves is illustrated in WO 9958245 (Amersham Pharmacia Biotech AB, Larsson, Allmér, Andersson) which describes hydrophilic channels in which liquid transport is hindered by hydrophobic surface breaks), WO 9955827 (Amersham Pharmacia Biotech AB, Tooke) which describes a mnicrostructure:
conduit 1-chamber 1-conduit 2-chamber 2-conduit 3
in which a valve function is suggested before each conduit/chamber if the cross-sectional areas of the conduits are decreasing (channel 1>channel 2>channel 3) and/or the internal surface hydrophobicities are increasing (channel 1<channel 2<channel 3), WO 0146465 (Gyros AB) which describes a centrifugal based system and suggests an inner valve for directing a single liquid aliquot into a predetermined branch by changing the spinning speed, and U.S. Ser. Nos. 09/812,123, 09/811,741 and corresponding PCT-applications (Gyros AB) (including SE priorities) give a similar system as in WO 0146465 for directing two aqueous liquid aliquots containing different amounts of an organic solvent into different branches. The present application bases its priority on these US and SE filings.

See also WO 0147638 (Gyros AB), and WO 0040750 (Amersham Pharmacia Biotech AB). WO 0185602 (Åmic AB & Gyros AB) suggests that inner valves based on hydrophobic surface breaks can easily be created in a rectangular microchannel having projections and/or depressions between length-going edges by applying a hydrophobizing liquid agent between the projections and/or in the depressions. WO 9615576 (David Sarnoff Res. Inst.) and EP 305210 (Biotrack) describe capillary valves that are based on an abrupt increase of the cross-sectional area of a microchannel, typically combined with a dam in the bottom part of the channel. Similarly WO 9807019 (Gamera) describes a capillary valve that is based on a change of at least one lateral dimension of a microchannel.

Type 3c Valves (geometric valves) have been suggested in form of linked U/Y-shaped microconduits for centrifugal based systems (e.g. WO 0146465 Gyros AB, and WO 0040750 Amersham Pharmacia Biotech AB).

Mixing Unit.

Units for mixing liquid aliquots within microfluidic devices have previously been described. These units have been based on
(a) mechanical mixers (e.g. WO 9721090, Gamera),
(b) creation of turbulent flow in a microcavity by two incoming liquid flows (e.g. WO 9853311, Gamera),
(c) creation of a laminar flow in the inlet end of a microconduit and mixing by diffusion during the transport in the microconduit (e.g. U.S. Pat. No. 5,637,469, Wilding & Kricka) etc.

WO 0146645 (Gyros AB) gives a structure that is said to facilitate mixing in centrifugal based systems (page 10, lines 15-16).

U.S. Pat. No. 4,279,862 (Bretaudiere et al) suggests a centrifugal based system with a mixing channel which has separate means for creating turbulence. This patent gives no information about dimensions and the particular problems encountered when downscaling into the nano-litre range.

Unit for Defining a Plurality of Liquid Aliquots in a Microfluidic Device.

According to the inventors knowledge publications related to this topic are rare. U.S. Pat. No. 6,117,396 (Orchid) gives a non-centrifugal gravity based microfluidic device in which a common reagent channel is used both as an overflow channel and as a reagent fill channel. A plurality of parallel volume metering capillaries is connected at different positions to the reagent fill channel from below.

Downward and Upward Bents in Microchannel Structures.

Microfluidic devices with a microchannel structures that comprises a part that bents towards a lower level (downward bent) and/or a part that bents towards a higher level (upward bent) have been described previously. Downward and upward bents has been linked to each other in series. Bent structures for centrifugal based system have been used for metering liquids, process chambers etc.

The microchannel part in a bent may or may not have an enlarged cross-sectional area.

If gravitational force, centrifugal force and other-inertia forces are used for transporting liquids, downward bents have been used for retaining liquid (valve function). Liquid retained in this way has been subjected to distinct process steps, e.g. chemical or biochemical reactions, affinity reactions, measurement operations, volume metering etc. These kinds of process steps have been carried also while the force is applied, for instance during spinning of a circular disc.

Downward bents have had an opening in its lower part that via a connecting microconduit has rendered it possible to transport a retained liquid aliquot from the bent further into another part of the microchannel structure, for instance to another downward bent. In order to control the transport, the connecting microconduit typically has been equipped with a valve function of the kinds discussed elsewhere in this specification, preferably an inner valve. One of the shanks of a downward bent typically has communicated directly or indirectly with an inlet port or with a separate vent.

Upward bents typically have had a vent in its top part (top vent). In certain variants one of the shanks of an upward bent have been connected to one of the shank of a downward bent.

By the terms U-shaped and Y-shaped structures are meant any downward bent structures irrespective of the angles between the shanks at the lowest part or at a branching point (only Y-shaped forms).

Bents have been smooth (curved) or sharp (angled).

Further details about previously known bent structure are given in: WO 9958245 (Amersham Pharmacia Biotech AB);

WO 9955827 (Amersham Pharmacia Biotech AB); WO 0147638 (Gyros AB); WO 0146465 (Gyros AB); WO 0040750 (Amersham Pharmacia Biotech AB); U.S. Ser. Nos. 09/812,123, 09/811,741 and corresponding PCT application (Gyros AB); and SE appl 004296-0, filed Nov. 23, 2000 (Gyros AB, Gunnar Kylberg). Bent structures have also been indicated in the scientific presentations made by Gyros AB.

Controlled Evaporation.

Drying of a microfluidic structure after its use has been suggested for MALDI-MS applications (U.S. Pat. No. 5,716,825, Hewlett Packard; U.S. Pat. No. 5,705,813, Hewlett Packard). The suggested microfluidic structures have had inlet ports and outlet ports. Evaporation from specifically designed openings (outlet ports) has been described in (U.S. Ser. Nos. 09/812,123, 09/811,741 and corresponding PCT applications filed with US and SE priorities. See also Magnus Gustavsson et al (ASMS 2001) (references given above)

Liquid Transport Initiated by Imbibing.

Imbibing means that liquid transport is initiated in the edges of micro channels. See for instance Dong et al (J. Coll. Interface Science 172 (1995) 278-288) and Kim et al (J. Phys. Chem. B 101 (1997) 855-863). See also EP 305210 (Biotrack).

Imbibing renders it difficult to retain a defined volume of a liquid in a desired microcavity for a longer period of time in case there is a microchannel having a length-going edge directly connected to the microcavity. If the microchannel is connected to ambient atmosphere, for instance via an inlet port, imbibing will promote evaporation and irreversible loss of a predispensed liquid volume. The creeping of liquid in edges from one microcavity is called wicking. Surface modifications (physical as well as chemical) that counteract wicking are called anti-wicking means. Anti-wicking means in the form of hydrophobic surface break between two length-going edges have been described previously (WO 9958245, Amersham Pharmacia Biotech AB).

Imbibing has also been utilized to promote liquid penetration into microchannel structures by including edge/corner structures associated with inlet ports. See U.S. Pat. No. 4,233,029 (Eastman Kodak) and U.S. Pat. No. 4,254,083 (Eastman Kodak).

Definition of the Volume of Liquid Aliquots that are to be Used in a Microfluidic Structure.

The definition of the volume of a liquid aliquot to be distributed to a microchannel structure can take place outside the structure and/or within the structure. The alternative to be used depends on different factors: (a) kind of dispenser, (b) accuracy needed, (c) kind and amount liquid to be dispensed, (d) process protocol to be run within the structure etc.

External dispensing means for μl-volumes and smaller typically utilizes syringe pumps, ink-jet type dispensers, pins or needles. A suitable ink-jet type dispenser of the flow-through type is described in U.S. Pat. No. 6,192,768 (Gyros AB). Systems utilizing pins and needles are described in U.S. Pat. No. 5,957,167 (Pharmacopea) and WO 0119518 (Aclara). See also U.S. Ser. No. 10/004,424 (Gyros AB).

Internal volume defining units are previously known. U.S. Pat. No. 6,117,396 (Orchid), for instance, gives a non-centrifugal gravity based system in which a common reagent channel may act as an overflow/filling channel along which there is spaced a plurality of volume metering capillaries for μl-volumes. Internal units for metering volumes in centrifugal based system have been described in WO 9843311 (Gamera), WO 0146465 (Gyros AB) and WO 0040750 (Amersham Pharmacia Biotech AB).

Separation of Undesired Particulate Material from a Liquid in a Microchannel Structure.

In non-centrifugal based systems this kind of separation typically has utilized mechanical filters. See for instance (U.S. Pat. No. 5,726,026, Wilding & Kricka). In centrifugal based systems chambers enabling sedimenting-decanting have been suggested for fractionating μl-volumes of whole blood into red blood cells, buffy coat and plasma (WO 9843311 (Gamera).

Means for Driving a Liquid Flow Through Microchannel Structures.

The liquid flow may be driven in microfluidic structures by distinct means that either is present on the substrate or is external to the substrate. The former variants typically means liquid flow created by electroendosmosis, by micropumps that are present on the substrate, expanding gas etc. The latter variants typically mean external pressure-generating means that create a liquid flow that is in fluid communication with the microchannel structure. Another alternative is to use forces such as capillary forces and inertia force including gravitational force and centrifugal force. In this latter case no means for moving the liquids is required in the microchannel structures or in the substrates carrying the microchannel structures.

Variants in which the microchannel structures are oriented from an inward position to an outward position in relation to an axis of symmetry of a substrate as described above are typically combined with a spinner that is capable of spinning the substrate around the axis of symmetry. This kind of spinners should be able to create the necessary centrifugal force for driving the liquids through at least a part of a microchannel structure. The centrifugal force may be utilized in combination with a second liquid aliquot to create a sufficient local hydrostatic pressure within a structure to drive a first liquid aliquot through an outward (downward) and/or an inward (upward) bent of a microchannel structure. See for instance WO 0146465 (Gyros AB). Typically spinning speeds are within the interval 50-25000 rpm, such as 50-15000 rpm. The spinning speed within a given protocol may vary and depends on the part structure that is to be passed by a liquid, for instance. A rapid passage for instance will require a higher speed and a slow or controllable passage a lower speed. In case the microfluidic device contains a plurality of microchannel structures that are to be run in parallel, it may be beneficial to start the passage of a particular structural unit with a short pulse of increased spinning followed by a slower spinning. Plurality in this context refers to the number of microchanmel structures given above.

Detailed Description of the Main Subaspects of the Invention (Structural Units 1-12).

The characteristics, such as dimensions, volumes, liquid contact angles, manufacture etc, and their preferences described above in the context of microconduits, microchambers, microcavities, microchannel structures etc also apply to the various functional units given below, if not otherwise indicated.

Inlet ports typically have hydrophobised areas to direct applied liquid into the ports. See for instance FIGS. 6 and 13. Local surface breaks that are hydrophobic for aqueous liquids are represented by straight or bent rectangles. They are primarily present for controlling liquid flow, e.g. in valves (inner valves), in anti-wicking means, in vents and for directing liquid inwards the structures in inlet ports.

In the figures circles represent openings to ambient atmospheres (inlet port, outlet ports, vents etc).

Unit 1 (Split Flow)

The first subaspect of the invention is a microfluidic device comprising a microchannel structure in which there is a structural unit accomplishing split flow as discussed for the first objective.

Unit 1 is illustrated in FIG. 2.

Unit 1 enables selectively directing a first liquid aliquot (aliquot 1) into one branch (202) and a subsequent liquid aliquot (aliquot 2) into another branch (203) of a common microconduit (201). The expression "selectively directing" in this context comprises that more than 50%, such as more than 75% or essentially 100% of at least one aliquot goes into the same branch. The composition of the aliquots may be identical or different.

At least one of the aliquots should have a surface tension, which is $\geq 5$ mN/m, such as $\geq 10$ mN/m or $\geq 20$ mN/m.

As illustrated in FIG. 2 the unit comprises
(a) an incoming microconduit (201) which in its downstream part divides into at least two microconduit branches (202, 203) at a branching point (204), and
(b) an inner valve function (205a,b) associated with one or both of the branches (202,203).

The inlet end (206) of the incoming microconduit (201) communicates in the upstream direction with an inlet port (not shown) of the microchannel structure. Each of the two branches (202 and 203, respectively) communicates in downstream directions with separate parts of the microchannel structure, for instance separate outlet ports (not shown). Valve parts (205a,b) may be present close to the branching point (204) and/or in more remote parts of a branch. Due to the presence of the inner valve function, the need to include mechanical valves or pumps to direct the aliquots is minimized.

The inner valve function comprises that either one or both of the branches have an inner valve including also the kind of valve defined for unit 9.

Factors that may influence an aliquot's selection of branch will depend on:
(A) Differences in chemico-physical properties between the aliquots, for instance surface tension,
(B) Differences in inner wall surface characteristics between the branches, and
(C) Directions of the branches relative to each other, etc.

In preferred variants of unit 1, the inner valve function at least partially is related to a difference between inner wall surface characteristics of the two branches. This difference may be local, i.e. be present in a circumferential zone in one or both of the two branches, or extend althroughout the branches.

Typical differences in surface characteristics include that one of the branches is more constricted or wider or otherwise more physically deformed than the other. Examples of other physical deformations are protrusions/projections and/or depressions/grooves that may be present in at least one of the branches. Physical deformations are typically present as ridges or valleys in one or more sidewalls and stretch between two edges. If the deformation starts from an edge this will mean that the deformation will be present in the two sidewalls that define the edge. If the deformation goes from one edge to another in the same sidewall this will also mean that the deformation is present in three sidewalls. Physical deformation in forms of ridges and valleys and the like are typically essentially perpendicular to the flow direction by which is meant $90° \pm 45°$.

The difference in surface characteristics may also include a chemical difference in the inner surface of the two branches. The inner surface of one of the branches may, for instance, expose more hydrophilic groups compared to the other (qualitatively and/or quantitatively).

The wettability relative a liquid, for instance water, may differ between the branches. In a typical case this means that
   the inner wall of branch (202) is more wettable by aliquot 1 than by aliquot 2, and
   the inner wall of branch (203) is more wettable by aliquot 2 than by aliquot 1.

In a preferred variant unit 1 comprises a downward bent, which in its lower part has an opening for downstream transport of liquid as illustrated in FIG. 2. One of the upwardly directed shanks of the bent corresponds to the common (incoming) microconduit (201) and the other shank to a branch (202). The opening in the lower part of the downward bent corresponds to the branching point (204) and is linked to a microconduit that corresponds to the other branch (203). An inner valve (205a), for instance in the form of a local surface break (non-wettable) and/or in the form of a change of geometric surface characteristics, may be associated with branch (203), for instance close to the branching point (204). Branch (202) typically is part of an upward bent, the top level of which is at a higher level than the lowest level of the downward bent and also at a lower level than the inlet end (206) of the incoming microconduit (201). Branch (202) may also contain an inner valve (205b). The upper part of the upward bent typically contains an opening to ambient air (top vent/inlet vent, 207) and/or broadens into a cavity permitting venting (not shown) of the top part of the bent. The top vent may be in the form of a venting conduit which preferably has an inner valve (207), for instance in form of a circumferential surface break (non-wettable). Under certain circumstances it may suffice if the top vent only has anti-wicking means of the type discussed elsewhere in this specification. The volumes of aliquots 1 and 2 are selected such that aliquot 2 is able to replace aliquot 1 in the downward bent by pushing it over the top part of the upward bent.

In preferred variants, a microchannel structure, which comprises unit 1, is arranged as discussed elsewhere in this specification for spinnable substrates; With respect to unit 1 and the variant shown in FIG. 2, this typically means that the extreme of the downward bent is at a larger radial distance than the extreme of the upward bent, if present.

The use of unit 1 for directing two liquid aliquots selectively into two different branches (202,203) of an incoming microconduit (201) comprises the steps of:
(i) Providing a microchannel structure comprising unit I as defined above and a first liquid aliquot (aliquot 1) and a second liquid aliquot (aliquot 2);
(ii) Introducing aliquot 1 and aliquot 2 in sequence into the unit via incoming microconduit (201), wherein aliquot 1 will pass out through branch (203);
(iii) Applying a driving force to pass aliquot 2 selectively through branch (202), by the assistance of the inner valve function of the unit.

At least one of the aliquots should have a surface tension, which is $\geq 5$ mN/m, such as $\geq 10$ mN/m or $\geq 20$ mN/m, tentatively aliquot 1.

For variants illustrated in FIG. 2 this will mean:
(a) Aliquot 1 is initially introduced into the downward bent. The upward direction of branch (202) and the surface characteristics associated with branch (203) will retain the aliquot in the downward bent (inner valve function).
(b) Aliquot 2 will replace aliquot I in the lower part of the downward bent and simultaneously move aliquot 1 downstream to branch (202).

(c) By applying the driving force on aliquot 2, the valve in branch (203) will be overcome and aliquot 2 passed into this branch.

For variants illustrated in FIG. 2, the driving force preferably is gravitational or centrifugal.

By properly adjusting the surface characteristics of an inner valve function in microconduit (203) in relation to properties of the liquid aliquots, it would be possible to drive aliquot 2 through microconduit (203) without increasing the driving force between steps (ii) and (iii) in the use of the variants illustrated in FIG. 2.

Other types of forces may also be used for transporting the aliquots in the inventive variants of unit 1. Examples are other kinds of inertia force, forces created by applying over-pressure at an inlet port or under-pressure at an outlet port, electrokinetic forces etc.

FIG. 2 illustrates the most preferred mode of unit 1 at the filing date.

Unit 2 (Mixing Unit)

The second subaspect of the invention is a microfluidic device comprising a microchannel structure in which there is a structural unit accomplishing mixing of liquid aliquots (unit 2).

This subaspect is based on our recognition that quick mixing of liquid aliquots that are miscible can take place by first collecting the aliquots in a microcavity, preferably under the formation of a phase system, and then permitting the aliquots to pass through a microchannel of sufficient length to permit homogeneous mixing.

Preferred variants of our mixing units are illustrated in FIGS. 3*a-c*. The variants shown are arranged as discussed above on a spinnable substrate (compare the arc-like arrangement). FIGS. 3*a-b* comprises four microchannel structures connected to each other by a common distribution channel.

In general terms unit 2 comprises an inlet arrangement (301) and a mixing microconduit (302) as described in prior publications. Between the inlet arrangement (301) and the mixing microconduit (302) we have introduced a microcavity (303) to precollect the aliquots to be mixed in the mixing microconduit (302). The precollecting microcavity (303) has an opening (323) in its lower part which opening is in register with the mixing microconduit (302). This precollecting microcavity may have various designs with one feature being that it should enable formation of a liquid interface between the two aliquots to be mixed. The flow direction should be essentially perpendicular at the interface, i.e. 90°±45°.

In addition to the mixing unit as such, FIGS. 3*a-b* show:

(a) A common distribution channel (304) as described for unit 3 below with an inlet port (305) with ridges/projections (306) as described for unit 10, an outlet port (307), and inlet vents (308) to ambient atmosphere via a common venting channel (309) and an air inlet (337). When the distribution channel is filled with liquid and a downward driving force is applied, liquid will be forced out through the microconduits connecting the distribution channel (304) with the microcavities (303). At the same time air will enter through the vents (308).

(b) A common waste channel (310) comprising outlet ports (311,312)

(c) Volume-defining units (313) as described for unit 11 and comprising anti-wicking means (314) as described for unit 7, an inlet port (315) with ridges/projections (316) as described for unit 10, and an overflow channel (317) ending in an outlet port (312) in the common waste channel (310); and (d) A microcavity (319) in which various kinds of processes may be carried out as discussed elsewhere in this specification, and an enlarged waste outlet conduit (320), which merges into the common waste channel (310).

Surface breaks (non-wettable) are represented by straight or arc-formed rectangles (e.g. 321*a,b,c* etc and 322, respectively).

The mixing unit of the present invention is characterized by comprising (a) the microcavity (303) with an outlet opening (323), typically in its lower part;

(b) an inlet arrangement (301) linked to the microcavity (303), and (c) a mixing microconduit (302) connected to the outlet opening (323).

The microcavity (303) shall have a volume sufficient to contain simultaneously the aliquots to be mixed.

The inlet arrangement is connected to the upper or lower part of the microcavity (303).

Preferably there is a valve associated with the mixing conduit (302), preferably close to its joint to microcavity (303). This valve function is preferably an inner valve of the same kind as discussed elsewhere in this specification, for instance in the form of a surface break (non-wettable) (321*b*). The valve may also be mechanical.

The inlet arrangement may comprise a common inlet microconduit for several aliquots and/or separate inlet microconduits (324 and 325) for individual liquid aliquots. The joint between these microconduits and the inlet openings are preferably located at the upper part of microcavity (303). In the upstream direction each of these inlet microconduits (324 and 325) communicates with an inlet port (305 and 315). Each inlet microconduit (324 and 325) may comprise a sub-microcavity permitting separate predispensing of a liquid aliquot to a microchannel structure before transport down into the microcavity (303). In FIGS. 3*a-b* one of these submicrocavities is microcavity (326) of the volume-defining unit (313) and the other an Y-shaped structure (327) a part of which belongs to the common distribution channel (304). Between each submicrocavity (326,327) and microcavity (303) there may be a valve function (321*d,c*, respectively) that enables for liquid aliquots to be transported into the submicrocavities (326,327) without leakage into the microcavity (303). The valve function at these positions is preferably an inner valve of the same kind as discussed for the valve functions (321*a,e*) associated with the mixing microconduit (302), e.g. a surface break (non-wettable) (321*a,b*).

As illustrated in FIGS. 3*a-b* the mixing conduit (302) may have various forms. It may be a single channel that is meandering or coiled in order to save space as suggested in FIG. 3*a*. It may also be built up of a chain of interlinked small microcavities (328), each of which has a smoothly increasing cross-sectional area from the inlet end and a smoothly decreasing cross-sectional area when approaching the outlet end as suggested in FIG. 3*b*. FIG. 3*b* also illustrates that these small microcavities can be of continuously increased breadth from their inlet and outlet ends with the steepest increase from the outlet end (droplet-shaped breadth).

When the liquid aliquots are introduced into microcavity (303) there should be formed a phase system in the microcavity. Each aliquot should be represented by a liquid phase. The flow direction out of the microcavity (303) should be essentially perpendicular to the interface between the phases. During passage of the phase system into the mixing microconduit (302), the upper phase is typically entering in the center of the microconduit and the lower phase next to the inner wall. Mixing will occur during the transport in the microconduit (302), probably due to the fact that the center of the liquid flow will have a higher flow rate than the peripheral part next to the inner wall of the mixing conduit. This means that the two aliquots repeatedly will replace each other in the front position while traveling through the mixing microconduit. This may be the reason for the quick and efficient mixing that is accomplished in the inventive mixing structure. If the mixing microconduit (302) is of sufficient length in relation to the flow rate and the constituents of the aliquots, complete mixing will have occurred at the end of the mixing microconduit (302). Sufficient length typically means that the phase system should have a smaller volume than the volume of the mixing microcoduit (302).

FIG. 3c shows a third variant of the inventive mixing unit. This variant has a microcavity (329) corresponding to microcavity (303) in FIGS. 3a-b. The microcavity (329) comprises an upper downward bent (330) and a lower downward bent (331) and a channel part (332) going from the lower part of the upper bent (330) to the lower part of the lower bent (331). In the lower part of the lowest bent (331) there is an opening (333) leading into a mixing microconduit (334). Preferably there is a valve (335) in the mixing microconduit (334), typically close to the opening (333). This valve preferably is an inner valve for instance comprising a change in surface characteristics (non-wettable surface break). FIG. 3c in addition shows inlet vents to ambient atmosphere (336a-d) at top positions of the bents. When filling the downward bents with aliquot 1 and aliquot 2, respectively, a liquid interface can be formed in the communicating microconduit (332). By applying a downwardly directed driving force the two aliquots will be forced into the mixing microconduit in the same manner as for the variants described in FIGS. 3a-b.

The microcavity (329) of FIG. 3c may be part of two aligned common distribution channels of the same kind as outlined in FIGS. 3a-b.

In preferred variants, a microchannel structure comprising unit 2 is oriented on a substrate having an axis of symmetry (spinnable) as discussed elsewhere in this specification. The flow direction through the outlet opening of microcavity (303) is typically oriented essentially outward in relation to the axis of symmetry (spinning axis).

The use of unit 2 comprises a method for mixing two or more liquids within a microfluidic device comprising a microchannel structure. The method is characterized in comprising the steps of:
(i) providing a microchannel structure comprising unit 2 as defined above;
(ii) introducing the aliquots via the inlet arrangement into microcavity (303), preferably to form a phase system therein;
(iii) applying a driving force to transport the phase system through mixing microconduit (302);
(iv) collecting the homogenously mixed aliquots at the end of the mixing microconduit (302) for further transport and/or treatment within the microchannel structure.

If submicrocavities (326,327) are present in the inlet arrangement (301), the aliquots to be mixed may be individually predispensed to these submicrocavities before the driving force for transport into microcavity (303) is applied.

The rules for selecting driving force are the same as discussed for unit 1.

At least one of the aliquots should have a surface tension, which is ≧5 mN/m, such as ≧10 mN/m or ≧20 mN/m.

Common waste channel: In FIGS. 3a-b the common waste channel (310) have supporting means for minimize the risk for collapse due to the breadth of the channel. The surface break (327) improves the emptying of the overflow channel (317) and facilitate its refilling.

Unit 3 (Unit for Forming a Plurality of Liquid Aliquots of Defined Volumes within a Microfluidic Device).

The third subaspect of the invention is a microfluidic device comprising a microchannel structure in which there is a structural unit (unit 3) accomplishing metering one, two or more liquid aliquots (plurality of aliquots).

This subaspect is based on our recognition that:
(a) the relative loss of liquid by evaporation may be significant when dispensing small liquid aliquots, in particular nl-volumes, to individual microchannel structures in a microfluidic device, and
(b) the compositions of metered aliquots may vary significantly for systems utilizing a common reagent fill channel from which metering is done in parallel to a plurality of metering microcavities when the cross-sectional dimension of the channel is decreased.

Unit 3 presents a solution to these problems and makes it possible to reproducibly meter a number of smaller aliquots within the same microfluidic device and transport of these aliquots in parallel into separate microchannel structures of the microfluidic device or into separate parts of the same microchannel structure. The aliquots may be identical or different with respect to size, composition etc.

Unit 3 is represented in FIGS. 4a-c which show variants that are arranged in a substrate having an axis of symmetry as discussed above. In these figures the distribution unit as such is encircled and labeled (400).

The unit comprises
(a) a continuous microconduit (401) containing an upper part at each end (end parts, 402, 403) and therebetween alternating lower and upper parts (404a-f and 405a-e, respectively);
(b) the number of upper parts including the end parts is n and the number of lower parts is n−1 where n is an integer ≧2;
(c) each of the upper parts (402, 403, 405a-e) has means for venting (top vent, inlet vents) (406a-g) to ambient atmosphere;
(d) each of the lower parts (404a-f) has an emptying opening which in a downstream direction via a connecting microconduit (407a-f) communicates with a substructure of a microchannel structure and/or with a corresponding substructure of another microchannel structure;
(e) each of the connecting microconduits (407a-f) has a valve (408a-f);
(f) an inlet port (409) is connected to the continuous microconduit (401) directly or indirectly at one of the upper parts (402, 403, 405a-e), preferably via one of the end parts (402 or 403);
(g) an outlet port (410) is connected to the continuous microconduit (401) directly or indirectly at another upper part (402, 403, 405a-f), preferably via one of the end parts (402 or 403) (which is not connected to the inlet port).

In a lower part (404a-5), the continuous microconduit (401) is preferably shaped as a downward bent. This kind of bents includes that the microconduit in the bent is enlarged to a microchamber or microcavity. Similarly an upper part is preferably in the form of an upward bent of the channel. This part may also include an enlargement similar to the downward bent. The cross-sectional area of the continuous microconduit (401) is typically of constant size and/or shape along the length of the continuous microconduit.

The inlet ports (409) and the outlet ports (410) are typically at a lower level than the extremes of the upward bents and may even be at a lower level than the extremes of the lower parts (404) and/or than a desired part of the individual microchannel structures that are downstream the lower parts (404) (for instance at a lower level than a waste outlet port).

The liquid aliquot is preferably transported from an inlet port (409) to an outlet port (410) of the continuous microconduit (401) by capillarity meaning that the liquid contact angle in this part of the microchannel structure has to be well below 90°, i.e. preferably $\leq 40°$, such as $\leq 30°$ or $\leq 20°$.

In the preferred variants the continuous microconduit (401) has meander-form.

The integer n is preferably $\geq 2$, such as 3, 4, 5, 7, 8, 9, 10, 11, 12 or more.

All the joints between a connecting microconduit (407a-f) and a lower part (404a-f) are preferably located at the same level and/or at the lowest part of a downward bent. The valves (408a-f) in the connecting microconduit (407a-f)) preferably are inner valves that may be closing or non-closing.

All the top vents (406a-g) are preferably located at the same level on the upward bents (402, 403, 405a-e). Each top vent (406a-g) comprises an opening in an upper part (402, 403, 405a-f) of the continuous microconduit (401) and possibly also a microconduit. The top vent may have an inner valve and/or may be equipped with anti-wicking means in case the top vent has a length-going edge that might promote imbibing and evaporation of liquid. For anti-wicking means see e.g. unit 7, below. The top vents may be connected via a common venting channel (411) and an inlet (425) to ambient atmosphere.

Unit 3 is primarily intended for distributing (n–1) liquid aliquots to (n–1) microchannel structures or (n–1) part structures of a microchannel structure. The volume between two close top vents (406a-g) will define the volume of the aliquot to be dispensed through the connecting microconduit (407a-f) between these top vents (segment). By varying the depth and/or width between different segments, one can envisage that the volumes dispensed through different connecting microconduits (407a-f) can differ in a controlled manner.

By first filling the continuous microconduit (401) with liquid between its end parts (402 and 403) and then forcing liquid to pass through the connecting microconduits (407), the liquid aliquots between close top vents will pass into separate connecting microconduits. Spillover between neighboring segments of the continuous microchannel (401) will be minimized due to the top vents and/or by the presence of anti-wicking means (426) in edges delineating lower walls in upper parts.

By filling the segments with the same liquid, for instance in one step, aliquots of the same composition will be dispensed through all the emptying openings.

FIG. 4b illustrates a non-meander form of unit 3 (straight form) in which the lower parts (404a-h) are in form of microcavities that are connected to each other via upper parts (405a-g). At the end of the continuous microconduit (401) there are also upper parts (402,403) via which an inlet and an outlet port may be connected (409 and 410, respectively). Means for venting (406a-i) the continuous microconduit (401) are associated with upper parts of the continuous microconduit, for instance in the conduit parts (405-a-g) and/or in the end parts (402-403). The lower part of each microcavity (404a-h) has an outlet opening to which a connecting microconduit (407a-h) with a valve function (408a-h) is associated. There may also be anti-wicking means at both sides of the microcavities (404a-h) in edges (rectangles, 426a-i) that extend down into a neighboring microcavities (404a-h). The anti-wicking means may be of the same kind as discussed elsewhere in this specification.

FIG. 4c represents a variant of unit 3, which will enable distribution of aliquots of different compositions to individual microchannel substructures. The distribution unit as such is encircled (400). Upstream the distribution unit (400) there is a microchannel substructure (411), which will enable filling segments between close top vents (406a-d) of the continuous microchannel (401) with liquid aliquots of different compositions, if so desired. In order to accomplish this, substructure (411) comprises a volume-defining unit (412), which is capable of metering a liquid volume that is equal to the volume of the segment between two close top vents (406a-d) in the continuous microchannel (401). If the volumes of the segments are different, it may be necessary to include different volume defining units in the substructure. In FIG. 4c, the substructure (411) upstream the distribution unit (400) may comprise further functionalities in addition to the metering functionality. Thus substructure (411) may comprise a first downward bent (413) which has one of its shanks (414) connected to the end part (402) of the continuous microchannel (401) and the other shank (415) connected to the lower part of a second downward bent (416) that in turn is connected to a volume-defining unit (412) at the upper part of one of its shanks (417). The other shank (418) of the second downward bent (416) is venting to ambient atmosphere via an inlet (427). The volume-defining unit (412) shown is of the same kind as unit 11 including an overflow system and has an inlet port (419) of the same kind as unit 10. The volume of the metering microcavity (420) of the volume-defining unit (412) is the same as in a segment between two close top vents (406a-d). The substructure (411) of FIG. 4c also comprises (a) a large waste chamber (421) with a relatively wide opening (422) into the lowest part of the first downward bent (413), and (b) a valve function (423) in the connection part between the first and second downward bent.

Due to the size of the waste chamber (421) there are supporting means in form of pillars (422) securing that its top and bottom are apart from each other.

The kind of design presented in FIG. 4c makes it possible to consecutively fill the segments between the top vents (406a-d) of the continuous microconduit (401) with liquid aliquots of different compositions and thus to distribute aliquots of different composition to the individual part structures connected to unit 3 via the connecting microconduits (408a-d). For instance with reference to FIG. 4c (and presuming that waste chamber (421) is closed or absent):

Step 1: Aliquot 1 is metered in the volume-defining unit (412) and transported to downward bent (413), for instance by spinning if the structure is placed on a circular disc.

Step 2: Aliquot 2 is metered in the volume-defining unit (412) and transported into the downward bent (413). This will move aliquot 1 to segment 1 (between top vents 406a and b) of the continuous microconduit (401).

Step 3: Aliquot 3 is metered in the volume-defining unit (412) and transported into the downward bent (413). This will push aliquot 1 to the next segment and place aliquot 2 in the first segment.

When the desired number of segments has been filled a downwardly directed driving force is applied to pass the aliquots through their respective connecting microconduit/valve (407a-d/408a-d).

In a simplified variant of the variants illustrated in FIG. 4c, the first downward bent is designed as a volume-defining unit, for instance by placing an overflow system at the same level as the top vents (406a-d) of the continuous microconduit (401) in shank (415).

By introducing a chemical functionality, for instance in the form of substructure comprising an inlet port followed by a reaction zone in front of unit 3, unit 3 may be used for collecting separate fractions between each pair of neighboring the top vents in the continuous microconduit (401 from liquids that have passed through the reaction zone. The size of a fraction will be defined by the volume between two close top vents in the continuous microconduit. Such fractions can then be further processed, for instance analysed, by taking them further down into the microchannel structure via the connecting microconduits (407*a-d*). With respect to FIG. 4*c*, such a zone suitably is positioned between the first and second downward bents (416 and 413, respectively), for instance combined with the valve (423)

The reaction zone may for instance comprise an immobilized reactant, for instance (a) a catalysts such as an enzyme, (b) a ligand capable of binding to component of a liquid which is to pass through the zone, (c) an affinity complex between a ligand and a binder etc. Based on the presence of particular components in the fractions that are collected one can analyse for features related to the zone as such or to the liquids applied, e.g. features of compounds present in the zone and/or a fraction.

Unit 3 is preferably present on a spinnable substrate of the kind discussed elsewhere in this specification. The continuous microconduit (401) is thereby oriented in an annular-like fashion around the spinning axis and occupies at least a sector of the annular zone defined by the continuous microconduit. The sector typically covers at least 0.5-10° and at most 360°. The lower parts (404) of the unit are directed outwards from the spinning axis and the upper parts (402, 403, 405) inwards towards the spinning axis.

The driving force is selected according to the same principles as outlined for unit 1.

The aliquot applied should have a surface tension, which is $\geq 5$ mN/m, such as $\geq 10$ mN/m or $\geq 20$ mN/nm.

Unit 4 (Annul Arrangements of Microchannel Structures)

The present inventors have recognized microchannel substructures and arrangements that are beneficial for increasing the total number of microchannel structures on a given planar substrate. The substrate in this unit is spinnable as discussed elsewhere in this specification. The objects of this subaspect are among others:

(a) to lower the risk for contaminating inlet ports with wastes from open waste outlet ports, and
(b) to reduce the drawbacks of a lower centrifugal force on a microchannel structures in an inner position versus microchannel structures in an outer position.

FIG. 5 illustrates this subaspect of the invention. The individual microchannel structures (501*a,b,c* etc, encircled) are defined under the heading "Technical Field" The characteristic feature is that:

(a) the microfluidic device comprises a plurality of individual microchannel structures (501*a,b,c* etc, encircled) which are
  (i) present in a substrate having a spinning axis (axis of symmetry); and
  (ii) arranged to define two or more annular zones (rings) (504*a,b,c*) around the spinning axis
    with each microchannel structure (501*a,b,c*) having a substructure (506*a,b,c*, 518, encircled) which is downstream the inlet port (505*a,b,c*) and which is capable of retaining liquid while spinning the substrate; and/or
    with inlet ports being located separate from the paths waste liquid aliquots leaving open waste outlet ports of the microchannel structures will follow across the surface of the disc when it is spun.

The term open primarily means open to ambient atmosphere. Each microchannel structure typically has an inlet port that is at a shorter radial distance from the axis of symmetry than the substructures that are capable of retaining liquid while spinning the disc.

The corresponding substructures of the microchannel structures of the same annular zone/ring or sector are present at the same radial distance while the corresponding substructures, if any, of other rings/zones are present at different radial distances.

In a variant the plurality of microchannel structures according to this subaspect can be divided into two or more subgroups (subgroups a, b, c etc) such that the
(a) corresponding substructures in microchannel structures of the same subgroup (annular zone) are positioned at essentially the same radial distance, and
(b) corresponding substructures in the microchannel structure of different subgroups (different annular zones) are positioned at essentially different radial distances.

The term "corresponding substructures" means substructures that have essentially the same function and the same relative position in the flow path of the microchannel structures which are compared. The substructure preferably is capable of retaining liquid while spinning the disc, for instance with a downward bent as desribed for substructures (506*a,b,c*, 518, encircled).

The center of the annular zones/rings typically coincides with the intersection between the spinning axis/axis of symmetry of the substrate. The annular zones of different subgroups may be partly overlapping or completely separate. The individual microchannel structures of one annular zone/ring may be equal or different. The individual members of an annular ring can be evenly spread over the zone or only occupy one or more sectors of the zone. See FIG. 5 in which the sector (507) is devoid of microchannel structures.

Feature *

The substructure (506*a,b,c*, encircled) that is capable of retaining liquid while spinning may be in the form of an outwardly directed bent (508) with two inwardly directed parts/shanks (509,510). See for instance the discussion about downward bents and the individual units above. One of these shanks (509) may communicate with an inlet port (505, encircled) in the upstream direction (inwards) and the other shank (510) may vent to ambient atmosphere either directly or indirectly, for instance via an inlet port or via an outlet port, for instance with an inlet vent or outlet vent function. The peripheral (lower part) of a bent (508) may have an opening connected to a microconduit (511), which is intended for downstream transportation of liquid. This opening may also communicate directly or indirectly with an outlet port for waste. This microconduit (511) may have a valve function (512) as described above, typically of type 1 or type 3a or b as defined above. Inner valves that are non-closing are preferred. Alternatively the downward bent may be devoid of a microconduit in its lower part for downstream transportation (518). The substructure may also be in the form of a chamber having an inlet directed upwards and an outlet downwards and associated with a mechanical valve in its outlet.

Feature **

This feature minimizes the risk that waste from an open waste outlet port shall contaminate inlet ports.

In a preferred variant this feature means that there are no open waste outlet ports at a shorter radial distance than an inlet port. Instead one or more waste outlets (513) from the individual microchannel structures of an annular zone/ring or sector are led in one or more common waste microconduits (514a,b,c) between two annular zones/rings or in the outer part of one annular zone/ring to a separate sector (507) of the disc in which there are no microchannel structures or inlet ports. In this sector the waste liquid is further transported, outward towards the periphery of the disc. Each common waste microconduit in this variant typically ends in an outlet port (515) that is at a larger radial distance than the inlet ports of the individual microchannel structures as shown in FIG. 5.

Alternatively the inlet ports and outlet ports may be on different sides of the microfluidic disc.

Feature ** in particular applies to variants in which both the waste outlet ports and the inlet ports open to ambient atmosphere on the same side of the disc.

An important feature of this innovative subaspect of the invention is that the microchannel structures of the same annular zone are divided into minor groups, and that microchannel structures of each minor group are connected to each other via a common inlet microcoduit or a common waste microconduit. This common microconduits extends essentially parallel to to the periphery of the disc and has fewer inlet ports and/or outlet ports, respectively than the number of microchannel structures in th group. In the variant illustrated in FIG. 5, there is anti-wicking means (516) between each pair of close microchannel structures connected to an inlet port via a common inlet microconduit (517). The anti-wicking means comprises a change in both geometric and chemical surface characteristics. In connection with the anti-wicking means there is also a vent to ambient atmosphere (not shown).

Unit 5 (Transport of Aliquots Back and Forth)

We have recognized that there are benefits to gain if one could transport a liquid aliquot back and forth in certain microchannel structures. A typical situation is when adsorbing a solute from the liquid aliquot to a solid phase which carries a ligand with affinity for the solute or when performing a chemical or biochemical reaction involving an immobilized reactant and a soluble reactant. In this kind of cases repetitive contact is likely to increase the chances for a reproducible adsorption/reaction and an increased yield.

The fifth subaspect of the invention is a microfluidic device comprising a microchannel structure in which there is a structural unit accomplishing back and forth transport unit (unit 5).

Unit 5 enables controlled transport of a liquid aliquot between two microcavities by wicking. An Y-shaped variant of unit 5 is illustrated in FIGS. 6a-c. In reference to FIG. 6a the unit comprises:

(a) two microcavities (601 and 602) and a capillary microconduit (603) connecting microcavity (601) and microcavity (602), (b) an inlet opening (604) which in the upstream direction communicates with an inlet port (not shown) and an outlet opening (605) which in the downstream direction communicates with an outlet port; said openings being present in microcavity (601), microcavity (602) and/or in capillary microconduit (603);

(c) a microconduit (606) permitting venting to ambient atmosphere in a dead end, if present, of the unit; and (d) possibly a valve function (607) associated with the outlet opening (605).

Particular variants of (b) are (1) both the inlet and the outlet opening (604 and 605) in the same microcavity, preferably with a vent to ambient atmosphere in the other microcavity, or (2) the inlet and outlet opening (604 and 605) in different microcavities, for instance in the inlet opening (604) in microcavity (601) and the outlet opening (605) in microcavity (602), and (3) one of the openings (604 or 605) in capillary microconduit (603) and the other opening in one of the microcavities (601 or 602), preferably with a vent to ambient atmosphere in the other microcavity, for instance with the inlet opening (604) in capillary microconduit (603) and the outlet opening (605) in microcavity (601) and the vent in microcavity (602).

FIG. 6a illustrates variant (3).

By the term "capillary microconduit" is meant that the microconduit in relation to microcavity (601) and the liquid aliquot has dimensions and surface characteristics such that the liquid aliquot will be transported from microcavity (601) to microcavity (602) by capillary action (wicking). This capillary action is enhanced by the presence of one or more edges starting in microcavity (601) or capillary microconduit (603) and going in direction towards microcavity (602). The capillary action can be enhanced, a) if a bed of particles is placed in the capillary microconduit (603), for instance in front of a constriction (608) that is capable of retaining the particles, and b) if microcavity (602) by itself is able to exert capillary suction, for instance by being segmented into capillary vessels as illustrated in FIGS. 6a-c.

In the variant shown in FIG. 6, the bed should reach up to the intersection between the inlet microconduit (609) and the capillary microconduit (603).

The venting microconduit (606) may be replaced with a transport microconduit in the case liquid is to be transported out of the unit via microcavity (602). It is the important to equip such a transport microcavity with venting means. The transport microconduit may be in the form of an upward bent with a top vent (inlet vent) at the upper part of the bent.

The inlet opening (604) typically communicates with the inlet port via an inlet conduit (609) in which there may be anti-wicking means and/or a valve (610) preventing wicking out of the unit.

The valve function (607) associated with the outlet opening of the unit shall prevent undesired exit of liquid from the unit. This valve may be closing or non-closing. The preference is for non-closing variants, if inertia force, such as centrifugal force, is used to move the liquid aliquot from microcavity (602) to microcavity (601). The same rules also apply to other valves in the unit.

Capillary microconduit (603) may have an infinitesmal length (including being absent).

In the case inertia force, such as gravitational force or centrifugal force, is used for driving the liquid from microcavity (602) to microcavity (601), microcavity (602) is typically placed at a higher level than microcavity (601). For spinnable substrates microcavity (602) should be at a shorter radial distance than microcavity (601). In cases other forces are used the two microcavities can be placed in the same order or the reversed order.

The use of the unit comprises the steps of:

i) providing the liquid aliquot and a microchannel structure comprising unit 5, ii) introducing the aliquot into one of the microcavities (601 or 602) depending on where the inlet opening (604) is, iii) permitting the liquid aliquot to be transported into the other microcavity and back to the microcavity into which it was initially introduced, iv) possibly repeating step (iii), v) applying a driving force that transport the aliquot from the unit via the outlet opening (605)

In this protocol the transport into the unit (step (ii)) is by applying a driving force and/or by capillary action. The driving force may be selected as generally discussed for the driving force in this specification. In preferred variants the driving force is inertia force with particular emphasis for centrifugal force. Transport from microcavity (601) to microcavity (602) utilizes interaction forces between the liquid aliquot and the surface of the inner wall of the unit and includes in preferred variants wicking/imbibing. Transport in the other direction may be accomplished by applying a driving force selected among the forces that can be utilized in step (ii).

If an immobilized reactant/ligand is placed in either of the microcavities (601 or 602) or in the capillary microconduit, the protocol will mean that the contact time and also reaction time can be increased by back and forth transport of a liquid aliquot. In the case the reactant is an affinity ligand for a solute, the use of unit 5 in many cases will improve the adsorption of the solute. This kind of reactant may be immobilized to particles that in turn are retained in front of a protrusion of an inner wall, for instance at (608).

In addition to what has been said above, FIG. 6a also shows a distribution system (611) as outlined for unit 3 and a common waste channel (612). Shadowed areas are surface breaks (hydrophobic breaks).

FIGS. 6b-c further illustrate the invention by showing unit 5 integrated into a complete microchannel structure and giving typical sizes (μm) of various parts and their position relative to each other.

Unit 6 (Structure Promoting Controlled Evaporation)

We have recognized that for certain protocols there will be benefits with a specifically designed functional unit from which controlled evaporation is promoted. Controlled evaporation can be used for concentrating a liquid aliquot that has been processed in a microchannel structure. Concentrating includes evaporation to dryness and/or crystallization of one or more constituents of a aliquot that has been processed in a microchannel structure etc.

The sixth subaspect of the invention is a microfluidic device comprising a microchannel structure in which there is a structural unit accomplishing controlled evaporation (unit 6).

One variant of unit 6 is illustrated in FIGS. 7a-b where FIG. 7a is a view of the unit from above and FIG. 7b is a cross-sectional view along the line A-A. The unit comprises
(a) an outlet port (701) may be in the form of a well (703) with an opening (702), a bottom (708) and side walls (707), and
(b) an incoming microconduit (704) that enters the well (703) and in the upstream direction communicates with an inlet port (not shown).

The opening (702) may have various shape, such has rectangular, rounded etc. It may be elongated, circular, compact such as in a regular polygon with the same size of all sides etc. The well (703) may have a deeper central part (705) and a shallow peripheral part (706). Either one or both of these parts may slope inwards towards the center of the well. The microconduit (704) may enter the well in a side-wall (707) and/or in the bottom (708). In the latter case, entrance may be in the deeper central part (705) and/or in the shallow peripheral part (706). In certain variants, the microconduit (704) ends as a valley/depression/groove (709) in the bottom (708) of the well (703), preferably defining a constant depth in the valley/depression/groove (709) in relation to the remaining parts of the bottom (708) that then preferably are flat. The valley/depression may be branched and in form of a delta-like landscape. It may also be widening, for instance mimicking the shape a liquid drop, which is merging from the opening microconduit (704), and trumpet- or bell-shaped. The opening (702) may be surrounded by a non-wettable area (711 in FIG. 7c). The peripheral part (706) of the bottom (708) may also be non-wettable except for the open depression (709), if present.

The design with a deeper central part and a shallow peripheral part and/or wettable/non-wettable parts will promote concentrating the aliquot to a smaller area and possibly increase the sensitivity of a detection principle utilizing the concentrated form of the aliquot.

The bottom (708) of the well and possible also parts surrounding the well and/or the opening may comprise a conducting material in case the concentrated material is to be ionized after having been concentrated. This kind of wells have been suggested in U.S. Ser. Nos. 09/812,123, 09/811,741 and corresponding PCT-applications with SE priorities (Gyros AB) for use in energy desorption-ionisation processes from surfaces, e.g. MALDI. The conducting material may be at the surface or covered by some dielectric material (non-conducting material). Typical conducting materials comprise metals and/or conducting polymer materials. Typical non-conducting materials are made of plastics, ceramics etc. See also the corresponding International Patent Applications filed in parallel with this application.

FIG. 7c illustrates a variant of unit 6 that at the filing date was preferred for the application described in the preceding paragraph. The incoming microconduit (704) passes into the bottom (708) of the well (703) in uncovered form, which means it will look like a groove/depression (709) of constant depth that may widen in a drop-like manner (as shown) in the bottom (708). A non-wettable surface break (711) (hydrophobic) is positioned around the opening (702). In the variant shown this surface break extends as illustrated down into the bottom of the well and also covers parts of the sidewalls. Other parts of the well are wettable (hydrophilic). Further details are given in the applications referred to in the preceding paragraph.

The well may contain an affinity ligand that is capable of binding to a compound of interest in a liquid sample applied at the inlet port or in the processed sample. Such an affinity ligand is suitably immobilized to the bottom (708) by chemical means or by physical or bioaffinity adsorption. Affinity ligands comprise members of pairs such as antigens/haptens and antibodies and antibody active fragments, lectins and compounds containing carbohydrate structures, enzymes and their substrates/coenzymes/inhibitors, charged compounds and compounds having the opposite charge (ion exchangers) etc.

There may also be additional microconduits (710) that are connected to unit 6, typically to the bottom (708) or side-wall (707). One can envisage that this kind of extra microconduits (710) might be useful as outlet microconduits for liquid aliquots that do not contain a substance of interest but merely has to pass the unit 6. This kind of liquids may be illustrated with washing solutions and reconstituting solutions. The latter may be used in cases where a substance that has been concentrated and/or crystallized in unit 6 shall be dissolved in another solvent than the one removed in the unit by controlled evaporation. In cases where this kind of extra microconduits are present and used for letting liquid out from the, unit, they should connect to the well in its lowest part.

In preferred variants a microchannel structure, which contains unit 6, is oriented as discussed elsewhere in this specification on a spinnable substrate, typically with an inlet port positioned at a shorter radial distance than unit 6. The transport direction into the well (703) may be perpendicular to a side-wall (707) or at an angle $\leq 90°$. Evaporation is controlled among others by the rate at which a liquid aliquot merges into the inlet port. Evaporation will also depend on chemico-physical parameters of the liquid in the aliquot, for instance vapor pressure, surface tension etc, and the size and shape of the well. Transport may be caused by an applied driving force, for instance by spinning if the unit is present on a spinnable substrate. A too high spinning speed will increase the risk for drop/aerosol formation and counteract controlled evaporation.

Microchannel structures containing unit 6 may be combined with distinct means for promoting evaporation, for instance by increasing gas circulation around the outlet port that is formed as a well. This in particular applies to non-spinnable substrates. The means concerned can be illustrated with a fan. For spinning substrates the spinning as such gives mostly gives the appropriate gas circulation.

At least one of the aliquots applied should have a surface tension, which is $\geq 5$ mN/m, such as $\geq 10$ mN/m or $\geq 20$ mN/m Unit 7 (Anti-Wicking Means Based on a Change in Geometric Surface Characteristics).

We have recognized that in microfluidic devices there is a need for improved anti-wicking means relative a liquid. Anti-wicking means that are based on local changes in chemical surface characteristics in the walls between two close inner edges of a microchannel have been described previously (WO 9958245, Amersham Pharmacia Biotech AB, Larsson, Allmér, Andersson).

Anti-wicking means should in most cases counteract wicking in one direction but permit bulk liquid transport in the opposite direction through a microconduit.

We have now recognized that anti-wicking effects can be achieved and improved if a change in chemical surface characteristics is replaced with or combined with a change in geometric surface characteristics.

The seventh subaspect of the invention is a microfluidic device comprising a microchannel structure in which there is a structural unit comprising anti-wicking means (unit 7).

Unit 7 is illustrated in FIG. 8*a* and comprises:

(a) a microconduit (801) in direct communication with a microcavity (802) which comprises one, two or more length-going inner edges (803*a,b,c,d*) that start at or within the microcavity (802), (b) a change in geometric surface characteristics (804) in a zone of the inner wall of microconduit (801) outside the microcavity and associated with at least one of said one, two or more edges, (c) an optional change in the chemical surface characteristics (805), shown as a rectangle, surface break) which is physically associated with said change in geometric surface characteristics or is present in another edge or in a separate part of the same edge as the change in geometric surface characteristics.

The microchannel conduit (801) may be positioned either upstream or downstream microcavity (802).

The microconduit of FIG. 9 is rectangular and seen from above which means that only two edges (803*a-b*) are seen in the figure. The change in geometrical surface characteristics is a deformation in the form of an indentation, which may be ear-like. In the figure the identation is going in the side-wall from each viewable edge to the edge below. The inside of each ear-like indentation has a non-wettable (hydrophobised) surface, which corresponds to a change in chemical surface characteristics.

FIG. 8*a* shows unit 7 applied to a volume-defining unit as defined for unit 11 with an overflow channel (806), a volume-metering microcavity (807), an inlet port (808), and a valve function (809) at the outlet opening of the volume-defining unit.

FIGS. 8*b-c* gives alternative suggestions for changes in geometric surface characteristics of a rectangular microconduit (801) connected to a microcavity (802). The arrangement is seen from above in the same manner as for FIG. 8*a*. The change in geometric surface characteristics may be selected from indentations (810), protrusions (811) and an increase in the angle between the two inner wall parts defining a length-going inner edge. Also other physical deformations of the edges may be used. An indentation or a protrusion may be extending from an edge into one or both of the inner wall parts defining the edge. In most cases the deformation will also stretch across the wall between two length-going edges. An increase in the angle between two intersecting walls means in its extreme that the inner edge can be rounded within the zone carrying the antiwicking means but not rounded between the zone and the microcavity. Thus the microconduit (801) may locally be cylindrical.

The change in surface characteristics in anti-wicking means typically leads to decreased wettability by the liquid aliquot when going from microcavity (802) to the anti-wicking zone.

Typically the change in surface characteristics in length-going edges is at different distances (different zones) from microcavity (802) for at least two length-going edges of a microconduit. If the microconduit (801) has a four-edged cross-section (rectangular) with all four edges extending into the microcavity, opposite inner walls typically may have the change in surface characteristics at different distances from the microcavity in order to avoid formation of an inner valve function.

This subaspect of the invention (unit 7) also comprises inner valve functions (passive valves) in which a non-wettable surface break is combined with a change in chemical and geometric surface characteristics at essentially the same position along the length of all edges of a microconduit. In this case it may be beneficial that the change in chemical surface characteristics (non-wettability) extends to parts of inner walls that are immediately surrounding a change in geometric surface characteristics, i.e. non-wettability extends outside the deformation. To accomplish a proper valve function the antiwicking means in the valve should be located at the same position along the microconduit (801).

The microconduit (801) with anti-wicking means (804, 805) may be placed between the microcavity and a vent to ambient atmosphere, including an inlet port (808). In this case the anti-wicking means will lower undesired losses of liquid due to evaporation through the inlet port and/or the vent. The flow direction may also be selected such that the microconduit is used for transporting liquid into the microchannel structure. In this case the anti-wicking means will hinder undesired leakage into the structure. If the microconduit is branched it becomes important to equip both branches with anti-wicking means as discussed above. For branched microconduits one branch may be used to introduce liquid into the microcavity from an inlet port (808) and the other branch used as an overflow (806) channel and/or inlet channel for other liquids in both cases with a venting function (inlet and/or outlet venting function). Anti-wicking means will be beneficial for both branches.

This kind of inventive anti-wicking means is adapted to prevent wicking for liquid aliquots that have a surface tension, which is ≧5 mN/m, such as ≧10 mN/m or ≧20 mN/m.

Unit 8 (Unit for Creating a Liquid Front of Different Composition Compared to the Bulk Liquid Flow).

The present inventors have recognized that there may be advantages with introducing a liquid aliquot into a microcavity, if the front of the liquid has a different composition compared to the bulk. This kind of liquid transport can avoid problems associated with incomplete filling of a microcavity and also be used to protect a bulk liquid from oxidation reactions and evaporation losses during the dispensasation of μl- and in particular nl-volumes to microfluidic devices.

Figure 9A:
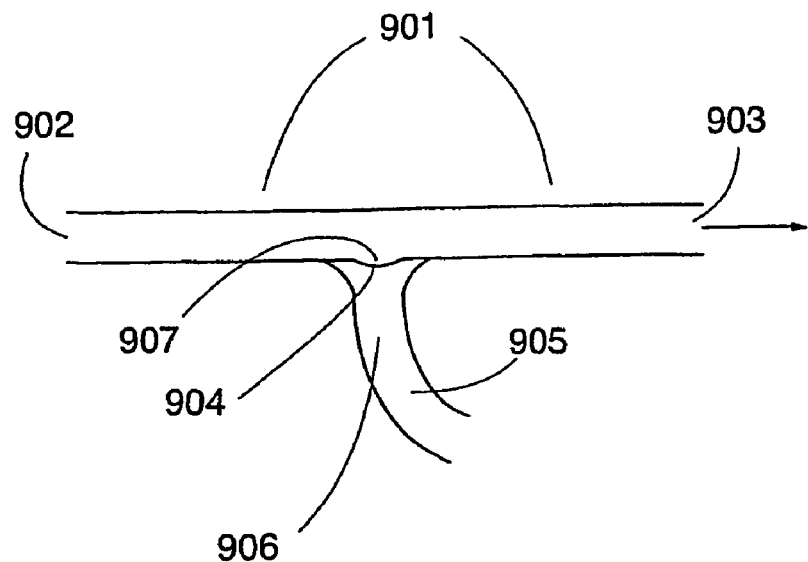
Figure 9B:
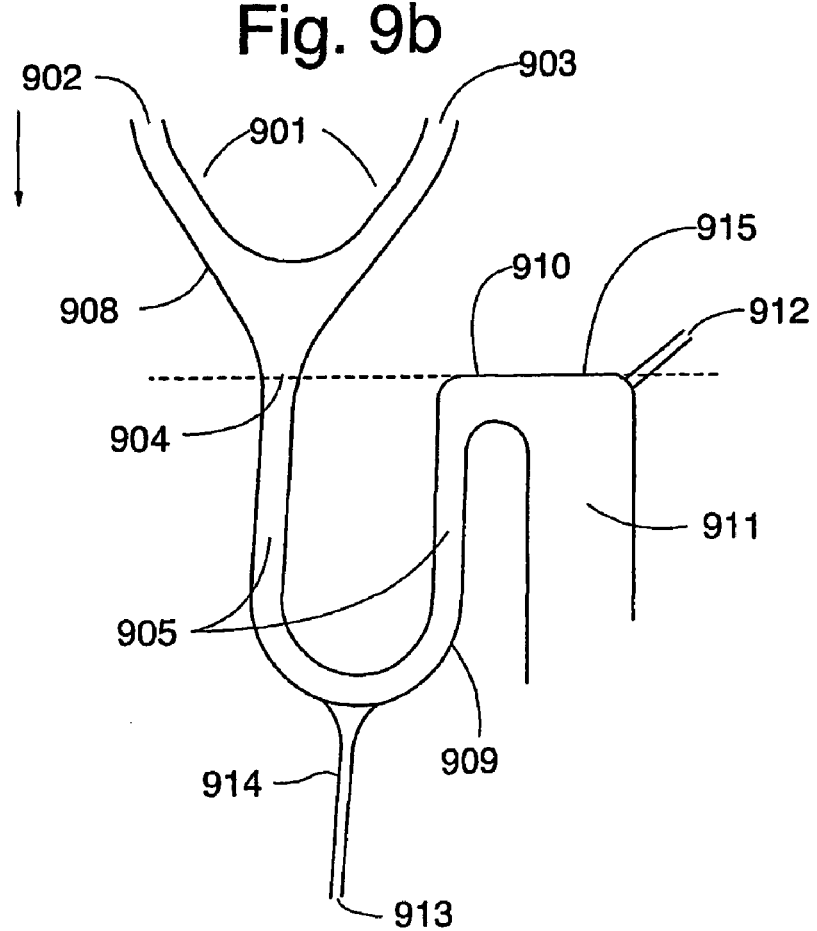

Unit 8 and its uses enables liquid transport in which the front zone (liquid 1) is of a different composition compared to the bulk (liquid 2). The unit is illustrated in FIGS. 9a-b.

In its simplest form (FIG. 9a) the unit comprises a microconduit (901) for transport of a bulk liquid (liquid 2). There is one inlet end (902), which communicates with an inlet port (not shown) of the microchannel structure comprising this unit, and one outlet end (903), which communicates with downstream parts of the same microchannel structure or directly with an inlet opening that can function as an outlet and/or inlet vent to ambient atmosphere. Along the microconduit (901) there is an opening (904) into a microcavity (905), which comprises the liquid (liquid 1) that will form the front zone. Liquid 1 (906) fills up the cavity (905) so that its meniscus (907) is in the opening (904). It has now been found that if an aliquot of liquid 2 is introduced via the inlet end (902) of the unit and passed by the opening (904), a small portion of liquid 1 will be placed as the front zone of liquid 2. This phenomenon is linked to the small dimensions of the microconduits.

Under certain circumstances the capillary barrier effect utilized in WO 9615576 (David Sarnoff Res. Inst.), EP 305210 (Biotrack), and WO 9807019 (Gamera) maybe used to retain the proper meniscus in the opening (904).

By selecting liquid 1 with proper surface tension in relation to the surface tension of liquid 2, the flow geometry of the front will be improved when the liquid transport enters microchannel parts that have irregularities, for instance corners that may create "dead ends" in microcavities and microchambers. Filling of this kind of microcavities may thus be more efficient.

A front zone of this kind will also protect liquid 2 from oxidation reactions caused by contact with ambient air and/or evaporation losses via the outlet end (903), e.g. via downstream connections to ambient atmosphere of the microconduit (901). In this latter variant there are advantages if liquid I is less volatile than liquid 2.

A design that is adapted to a spinnable substrate is illustrated in FIG. 9b. The main flow direction is indicated with an arrow. This variant may comprise two downward bents (908, 909) that are directed outwards from the spinning axis, and an upward bent (910) that is directed inwards towards the spinning axis (axis of symmetry). The first downward bent (908) has one shank comprising the inlet end (902) and the other shank the outlet end (903). The lower part of the first downward bent (908) comprises an opening (904) to a microcavity (905). This microcavity (905) comprises the second downward bent (909) and downstream possibly also the upward bent (910) followed by a waste chamber (911). The connection between the first and the second downward bent (908, 909) is via one of the shanks of the second downward bent (909) and the opening (904) in the first downward bent (908). The top part of the microcavity (905) is at essentially the same level as the opening (904) in the first downward bent (908). The venting function is typically an inlet vent positioned at a top part of the upward bent (910) (=top part of the microcavity (905)), if present. Since the top part is at essentially the same level as the opening (904), a meniscus of liquid 1 will be presented in opening (904) as long as the second downward bent (909) is filled with liquid 1 up to the top part (910) of microcavity (905). The waste chamber (911) will then function as an overflow channel.

If it is desired to transport liquid 2 out of the unit via outlet end (903), the appropriate valving in the microcavity (905) may be needed to reduce the risk that the driving force will transport liquid 2 out through the microcavity (905). Thus an inner valve, typically in the form of non-wettable surface breaks, may be placed in microcavity (905) in association with the opening (904). The non-wettability in this valve is selected such that liquid 1 is more prone to penetrate the valve than liquid 2.

In an alternative variant there is an outlet microconduit (914) at the lower part of the second downward bent (909). In this variant liquid 2 can be transported out from the unit via an opening in the lower part of the second downward bent (909). The variant also comprises a valve in the outlet microconduit (914) close to the intersection between the second downward bent (909) and the outlet microconduit (914). This valve prevents liquid 1 to pass through. It is preferably an inner valve typically based on non-wettable surface breaks that liquid 2 passes easier than liquid 1. The liquid front of liquid 2 that leaves the unit will be of the same composition as the bulk. The front of different composition will only be present in microconduit (901). The variant thus is primarily intended for protecting a dispensed liquid aliquot from evaporation and/or oxidation reaction during dispensation procedures that require some time, e.g. comprising dispensation to several inlet ports in series.

The lower channel wall (915) at the extreme of the upward bent (910) is preferably located at essentially the same level as the opening (904) in the microconduit (901) (not shown).

The driving force for transport of liquid 2 through microconduit (901) may be selected among those discussed elsewhere in this specification for the other units, with preference for centrifugal force in combination with microchannel structure comprising unit 6 being present on a spinnable substrate.

The use of this unit defines a method for creating a liquid front zone of different composition compared to a bulk liquid that is transported in a microconduit. This method is characterized by comprising the steps of:

(i) providing a microchannel structure comprising unit 9 with liquid 1 (906) placed in the microcavity (905) and exposing its meniscus (907) in the opening (904), (ii) introducing an aliquot of liquid 2 through the inlet end (902), (iii) applying a driving force so that the front of liquid 2 passes the opening (904) between the inlet end (902) and the outlet end (903) of the microconduit (901).

Unit 9 (Non-Closing Inner Valve)

In spite of the large number of various non-closing inner valves that at present are available there is still a need for improvements. As discussed elsewhere in this specification this kind of valves have primarily been based on changing either the geometric surface characteristics of microchannel inner walls or introducing local changes in the chemical surface characteristics (surface breaks). We have now recognized that more versatile valves can be accomplished if a non-closing inner valve combines geometric and chemical surface characteristics in a circumferential zone of a microconduit.

This kind of valves is primarily intended to control transport of liquid aliquots that have a surface tension, which is lower than normal.

At least one, preferably all of the liquid aliquots used should have a surface tension that is $\geqq 5$ mN/m, such as $\geqq 10$ mN/m or $\geqq 20$ mN/m.

The ninth subaspect of the invention is a microfluidic device comprising a microchannel structure in which there is a structural unit with a non-closing inner valve (unit 9).

Unit 9 is illustrated in FIG. 10 and comprises a microconduit (1001) with a defined flow direction (1002, arrow). The unit may be connected directly or indirectly via a part of the microconduit (1001) to a microcavity/microchamber (1003). The microconduit (1001) comprises a circumferential zone (1004) in which there is a non-closing inner valve function defined by (i) a change in geometric surface characteristics (1005) in at least one sidewall (1006) within the zone, and (ii) at least one sidewall (1007) that does not have having the change in geometric surface characteristics being non-wettable, preferably a sidewall opposing a side wall having a change in geometric surface characteristics.

The term non-wettable refer to chemical surface characteristics of the sidewall. Typically sidewalls containing the change in geometric surface characteristics are wettable at least in the circumferential zone In case the microconduit at the valve is rounded, a sidewall and the opposing sidewall simple refer to opposing parts of the circumferential zone. Such a part typically occupies 45°-150° of the circumferential zone comprising the valve function.

The change in geometric surface characteristics is typically a physical deformation (1005) that preferably extends across essentially the whole sidewall. If it connects to bordering/intersecting sidewalls a part of the bordering sidewalls will also contain a physical deformation.

The useful physical deformations are preferably in form of protrusions (projections) that extend as one or more ridges across the sidewall.

Physical deformations in the form of one or more projections/protrusions diminish the cross-sectional area in the circumferential zone such that the cross-sectional area becomes at most 75%, such as at most 25% or at most 25% or at most 10%, of the cross-sectional area of the microconduit (1001) upstream the circumferential zone containing the valve. Essentially the same figures may apply to the cross-sectional area that is immediately downstream the circumferential zone. The size and form of the cross-sectional area can be the same immediately upstream and downstream the circumferential zone.

The microconduit of unit 9 may be linked to a chamber-like structure (1003), by which is meant that the cross-sectional area at one end of the microconduit (1001) increases, for instance more than twice.

The length of the circumferential zone in which the change in geometric surface characteristics occurs is typically at least 10%, such as at least 50% or at least 100%, of the depth and/or of the width of the microconduit immediately upstream and/or immediately downstream the zone.

In use this subaspect of the invention defines a method for controlling transport of a liquid aliquot through a non-closing inner valve function. The method comprises the steps of:

(i) providing a microchannel structure comprising unit 9 as defined in the present specification and a liquid aliquot, preferably having a surface tension which is $\geqq 5$ mN/m, such as $\geqq 10$ mN/m or $\geqq 20$ mN/m;

(ii) introducing the liquid aliquot into the microchannel structure by assistance of a driving force of a magnitude that will not allow the aliquot to pass through the non-closing inner valve of unit 9; and (iii) increasing the driving force to a magnitude that is sufficient for transporting the liquid through the non-closing inner valve of the microconduit.

In step (ii) the front of the aliquot may be allowed to proceed into the microconduit up to the circumferential zone.

The driving force may be as described above. Typically the driving force is inertia force including gravitational forces and centrifugal forces. In case of centrifugal force the microchannel structure is typically oriented as discussed above for spinnable substrates. In step (ii) this kind of substrates is spun at a rate sufficient for overcoming the non-closing inner valve of unit 9. The kind of driving force may differ between steps (ii) and (iii). For instance capillary force or inertia force of the kind discussed elsewhere in this specification may be used in step (ii) while step (iii) may solely rely upon centrifugal force or an externally applied pressure.

Unit 10 (Inlet Unit with Means Supporting Liquid Entrance into a Microchannel Structure)

To include inlet ports having geometries facilitating penetration of liquids into a microchannel structure is previously known. See above. This aspect of the invention refers to an improvement that lowers the time for undesired evaporation of a liquid aliquot that has been dispensed to a microfluidic device of the same kind as the invention. The advantages are likely to be primarily related to dispensing and/or metering nl-aliquots within microfluidic devices.

The tenth subaspect of the invention is a microfluidic device comprising a microchannel structure in which there is an inlet unit promoting liquid entrance into a microchannel structure.

Figure 11B:
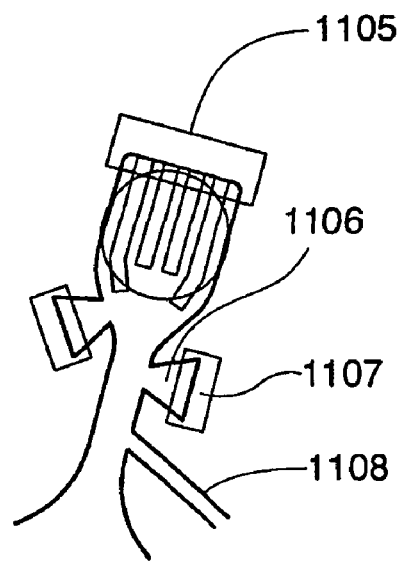

The unit is illustrated in FIGS. 11a-b. The unit comprises:

(a) an inlet port comprising a microcavity (1101) and an inlet opening (1102), and (b) an inlet conduit (1103) which is positioned downstream said microcavity (1101) and which communicates with the interior of the microchannel structure.

The inner wall of the microcavity (1101) comprises one or more grooves and/or projections (ridges/valleys) (1104) directed towards the connection between the inlet conduit (1103) and the microcavity (1101). The microcavity (1101) is tapered when approaching the inlet microconduit (1103).

The main purpose of the grooves and/or the projections is to increase the capillary suction in the inlet port. This will speed up liquid penetration and lower the time for undesired evaporation and loss of liquid during the dispensing operation.

FIG. 11b illustrates a variant comprising a non-wetting surface break (1105) in association with the rim of the inlet opening (1101), primarily at a side which is closest to spinning axis if the inlet port is located on a spinning substrate. This figure also illustrates a variant of unit 10 that comprises anti-wicking means downstream the inlet opening (1101). As antiwicking means in general, these antiwicking means may comprise changes in geometric surface characteristics (1106) and/or in chemical surface characteristics (1107).

This means that the projections may have a height that at maximum is equal to the depth of the microcavity (1101) but may be significantly lower as long as a sufficient capillary action is maintained in the inlet port.

The liquid to be introduced typically has a surface tension as discussed above.

The width of the inlet opening is typically smaller than the width of microcavity (1101) as illustrated in FIGS. 11a-b.

The inlet opening (1102) may have one or more edges directed inwards the port, preferably with an n-numbered axis of symmetry perpendicular to the opening. n is preferably an integer $\leq 7$, such as 3, 4, 5 or 6. See for instance U.S. Pat. No. 4,233,029 (Eastman Kodak) and U.S. Pat. No. 4,254,083 (Eastman Kodak).

The unit is typically combined with a dispenser that is capable of dispensing a liquid aliquot of $\leq 10$ µl, such as $\leq 1$ µl, or $\leq 500$ nl or $\leq 100$ nl or $\leq 50$ nl to the inlet port. The dispenser can be one of the dispensers generally described elsewhere in this specification.

Penetration after dispensing is typically taking place by utilizing capillary forces, interaction forces between a dispensed liquid and the inner surfaces in the inlet unit and other driving forces as discussed elsewhere in this specification. One example of suitable forces (other than capillary force) is inertia force including centrifugal force.

Microchannel structures comprising this kind of inlet port are in a preferred variant of this subaspect placed on a spinnable substrate and used as discussed elsewhere in this specification.

This kind of inlet unit is particularly well adapted to receive liquid aliquots that are inn form of particle suspensions.

Unit 11 (Definition of the Volume Liquid Aliquots in a Microfluidic Structure).

In spite of the previously known devices for metering liquid aliquots in the µl-range there is still a need for improvements, in particular with respect to the nl-range. The reason is that uncontrolled evaporation influences a smaller volume relatively more than a larger volume. This is further accentuated when a large number of aliquots are to be dispensed in sequence before the aliquots are further processed within a microfluidic device.

The present inventors have recognized these problems and designed a volume-metering unit (unit 11) to meter primarily nl-volumes of liquids. The unit can be integrated into microchannel structures of microfluidic devices.

The eleventh subaspect of the invention thus is a microfluidic device comprising a microchannel structure in which there is volume-defining unit enabling accurate metering of small volumes within a microfluidic device.

Unit 11 is illustrated in FIG. 12. The figure also illustrates the unit may comprise units 7 and 10. Unit 11 comprises (a) a volume-defining microcavity (1201), (b) an inlet microconduit (1202) which is connected to the microcavity (1201) via an inlet opening on the microcavity (1201), (c) an outlet microconduit (1203) which is connected to microcavity (1201) via an outlet opening in microcavity (1201), and (d) an overflow microconduit (1204), which is connected to an overflow opening on microcavity (1201).

The overflow opening is at a higher level than the outlet opening (1203) and the volume between these two openings defines the volume to be metered in the volume-defining microcavity (1201). This volume is typically $\leq 1000$ nl such as $\leq 500$ nl, $\leq 100$ nl or $\leq 50$ nl but may also be larger such as $\leq 10$ µl or $\leq 100$ µl or $\leq 1000$ µl.

The liquid typically has a surface tension as discussed above.

The overflow microconduit (1204) is typically communicating with ambient atmosphere at one or more positions, for instance at large waste chamber or waste conduit (1212), which is at a lower level than the connection between the overflow microconduit (1204) and the volume-defining microcavity (1201).

The outlet microconduit (1203) is used to transport a metered liquid aliquot further into the microchannel structure.

The volume-defining microcavity (1201) may have different forms, for instance comprise (a) one or more capillaries, (b) a downward bent structure with one shank acting as the inlet and the other shank ending in an upward bent that can be used as overflow microconduit (1204), and with the outlet microconduit (1203) being intended for transporting a metered aliquot further into the microchannel structure, (c) etc.

The cross-sectional area ($a_1$) in the volume-defining microcavity (1201) at the overflow opening is in preferred variants smaller than the largest cross-sectional area ($a_2$) between the overflow opening and the outlet opening. The ratio $a_1/a_2$ typically is $\leq 1/3$, such as $\leq 1/10$. This means a constriction of the microcavity (1201) at the joint between the overflow microconduit (1203) and the microcavity (1201), i.e. at the joint between inlet microconduit (1202) and volume-defining microcavity (1201).

The inlet microconduit (1202) upstream the overflow opening typically widens, for instance to an inlet port (1205), such as unit 10.

Between the volume-defining unit and a true inlet port there may other structural/functional units, for instance a unit for sample treatment such as for the removal of particulate materials.

Unit 11 may have a valve function (1206,1207,1208) associated with at least one of (a) the outlet opening of microcavity (1201), (b) the inlet microconduit (1202) upstream the overflow opening, and (c) the overflow microconduit (1204).

The valve may be a mechanical valve but is preferably an inner valve of the closing or non-closing type.

At least one of the inlet microconduit (1202), outlet microconduit (1203) and the overflow microconduit (1204) contains anti-wicking means of the kinds defined elsewhere in this specification. This variant of the 11$^{th}$ subaspect particularly applies if a microconduit has geometries promoting imbibing and wicking, for instance length-going edges. In FIG. 12 anti-wicking means (1209) are present in inlet microconduit (1202)

A microchannel structure comprising unit 11 may in its preferred variants be placed on a spinnable substrate as discussed elsewhere in this specification and equipped with valve functions (1203,1208), preferable inner valves that may be of the non-closing type. If the intention is to drive the liquid out of the over-flow channel (1204) before the metered aliquot is released via the outlet microconduit (1203), it becomes important to have a sufficiently large difference in radial distance between the overflow opening in the volume-defining microcavity (1201) and the ending of the overflow microconduit (1204) ($r_1$) in a waste chamber relative the difference in radial distance between the overflow opening and the valve (1206) in the outlet microcoduit (1203) ($r_2$). $r_1$ shall be essentially larger than $r_2$. This particularly applies if the valve function (1206) in the outlet microconduit (1203) is an inner non-closing valve. By selecting $r_1 \leq r_2$ it will be possible for the liquid in the over-flow microconduit to pass through the valve (1208) at a lower driving force (e.g. lower spinning speed) than required for the liquid in the volume-defining microcavity to pass through the valve (1206).

A variant that also is adapted to spinnable substrates comprises a downward bent with the volume-defining microcavity being a part of the lower part of the bent. The overflow microconduit typically is connected to one of the shanks of the downward bent and forms together with the lower part of this shank an upward bent. The upper part of the same shank vents to ambient atmosphere (inlet vent). An inlet port for sample (corresponds to 1205) may then be connected to the other shank of the same downward bent. The vent to ambient atmosphere may also have a sample inlet function. The outlet conduit with a valve is connected to the lower part of the downward bent (corresponds to 1203 and 1206, respectively). The overflow microconduit (corresponds to 1204) ends in a waste channel or waste chamber with a valve function (corresponds to 1208).

There are advantages with having the outlet opening (connected to the outlet microconduit (1203) on microcavity (1201) somewhat higher than the lowest part of the volume-defining microcavity. In such variants it will be possibly to sediment particulate materials and only collect a supernatant of defined volume through the outlet microconduit (1203). Sedimenting can be assisted by the use of centrifugal force (spinning).

The use of unit 11 defines a method for introducing metered liquid aliquots into microchannel structures. The method comprises the steps of:
(i) providing a microchannel structure comprising unit 11 and a liquid aliquot having a larger volume than then the volume to be metered in the unit;
(ii) introducing the liquid aliquot into the unit;
(iii) applying a driving force to move excess liquid out through the overflow microconduit (1204) and the metered volume through the outlet microconduit (1203) into the remaining part of the microchannel structure.

The driving force is selected as discussed above for the other units with preference for inertia force including gravitational force and centrifugal force when the substrate is spinnable.

The variant of unit 12 that is illustrated in FIG. 13 may also be used as a volume-defining unit, with the advantage that both the front zone and the tailing zone may be removed in the volume-metering process. This may often be advantageous because the front zone often is depleted of components that adsorb to surfaces.

Unit 12 (Separation of Particulate Material).

The microchannel structure of the present invention may contain a functional unit (particle separator) that enables separation of particulate material and further processing within the structure of either the liquid free of the particulate material or of the particulate material as such.

Particulate material is often present in samples and may interfere with or disturb downstream fluidics. This functional unit is therefore often positioned early in the microchannel structure, for instance linked directly to an inlet port. The separation unit may also be positioned after a processing unit and used to separate added particulate materials that has been or will be modified during the processing of a sample in the unit.

The twelfth subaspect of the invention is a microfluidic device comprising a microchannel structure in which there is a structural unit enabling separation of particulate material (unit 12).

Unit 12 is illustrated in FIG. 13. It comprises a microcavity (1301) in which there are:

(i) a lower part (1302) for particulate material,
(ii) an upper part (1303) for liquid free of particulate material,
(iii) an inlet opening (1304) at the top of the upper part (1303) of the microcavity (1301), and
(iv) an outlet opening (1305) between the lower part (1302) and the upper part (1303).

The inlet opening (1304) is intended for introduction of a liquid aliquot containing particulate material. This opening communicates in its upstream direction with an inlet port (1311) of the microchannel structure. Communication is via an inlet microconduit (1306). There may also be an overflow microconduit (1307) of the same kind as for volume-defining unit 11 associated with the inlet opening (1304). This overflow conduit ends in a waste chamber (1317*a*) or connects to ambient atmosphere, both of which alternatives are below the lower part (1302) of the microcavity (1301).

The outlet opening (1305) is intended for withdrawal of and further transport of liquid, which is free of particulate material, into other parts of a microchannel structure via an outlet microconduit (1308) attached to this outlet opening.

The lowest part of the lower part (1302) may be equipped with a second outlet opening and a second outlet microconduit (not shown), which is intended for withdrawal of particulate materials assembled in the lower part (1302).

The microcavity (1301) may be constricted (1309) at the outlet opening (1305) and/or the lower part (1302) may have a constant or diminishing cross-sectional area from the first outlet opening (1305) and downwards.

A valve function (1310) is preferably associated with outlet microconduit (1308), preferably close to the outlet opening (1305).

In a similar manner there may be a valve function (not shown) connected to the second outlet opening/outlet microconduit for withdrawal of particulate materials.

The overflow microconduit (1307), if present, is associated with a valve function (1313), for instance in the lower part of the over-flow microconduit (1307) or in the waste chamber (1317*a*) next to the end of the overflow microconduit.

The valve functions used in unit 12 may be selected amongst the various kinds of valves discussed elsewhere in this specification, with preference for inner valves, for instance of the non-closing type. The preferences are essentially the same.

The valve function in the overflow microconduit (1307), in the outlet microconduit (1308) and in the possible second outlet microconduit are designed such that liquid can pass through in the order given. This means that a metered volume free of particulate material can be collected through outlet microconduit (1308) after the particulate matter has sedimented into the lower part (1302) of the microcavity (1301). Possibly sedimentation is carried out after excess liquid has passed out through the valve (1314) in the overflow microconduit (1307) without letting liquid out through the first microconduit (1308) and second outlet microconduit (not shown).

The first (1305) and the second (not shown) outlet openings may be connected to separate funtional units of a microchannel structure. I these units liquid free of particulate material or the particulate material as such, respectively, can be further processed separately, e.g. assayed with respect to at least one component.

A microchannel structure, which comprises unit 12 is adapted to be placed on a spinnable substrate of the kind discussed elsewhere in this specification. The inlet opening (1304) is then placed at a shorter radial distance (higher level) than the first outlet opening (1305), which in turn is placed at shorter radial distance (higher level) than the second outlet opening (if present). When subjected to spinning the particulate material will sediment and assemble in the lower part (1302) of the microcavity (1301). If the difference in radial distance of the valve function (1313) at the outlet (1314) of the overflow microconduit (1307) is larger than the radial distance of the valve function (1310) in the first outlet microconduit (1305) or of the inlet opening (1304), the liquid in the overflow microconduit (1307) will leave at a lower spinning speed than the liquid in the first outlet microconduit (1308). This applies if the valve functions are inner valves of the non-closing type.

In use this subaspect of the invention defines a method for processing a liquid aliquot/sample containing particulate material in a microchannel structure that is present on a spinnable substrate as discussed elsewhere in this specification. Processing typically means that at least one component in the aliquot/sample is assayed. The method comprises the steps of:

(i) providing a microchannel structure comprising unit 12 and a functional unit in which either a component in the liquid as such (for instance a solute or the like) or in the particulate material can be processed, (ii) introducing an aliquot of the liquid sample into the unit, (iii) subjecting the microchannel to centrifugal force, to sediment the particulate material into the lower part (1302) of the microcavity (1301) and retain the liquid without particulate material in the upper part (1303) of the microcavity (1301), (iv) applying a driving force to transport (a) the particle-free aliquot through the upper outlet opening (1304) to the functional unit in which the particle-free aliquot can be further processed with respect to a component therein and/or (b) the particulate material through the second outlet opening to a functional unit in which this material can be further processed with respect to a component therein.

(v) running the process protocol that is associated with functional units that are downstream microcavity (1301).

The driving force in step (iv) may be inertia force such as gravitational force or centrifugal force or any of the other forces discussed elsewhere in this specification for transport of a liquid aliquot.

FIG. 13a also shows that there maybe anti-wicking means (1312) associated with the microconduit (1306) downstream the inlet port (1311).

The microchannel structures and functional units 1-13 have been manufactured and tested as outlined in the patent applications in the name of Amersham Pharmacia Biotech AB and/or Gyros referred to above.

Certain innovative aspects of the invention are defined in more detail in the appending claims. Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A microfluidic device that comprises a microchannel structure in which there are one or more inlet ports, one or more structural units downstream of one of the inlet ports, and one or more outlet ports, wherein the microfluidic device comprises a plurality of individual microchannel structures which are
   (i) present in a substrate having a spinning axis; and
   (ii) arranged to define two or more annular zones or sectors thereof around the spinning axis,
   each of said microchannel structure has a substructure which is downstream of the inlet port and which is capable of retaining liquid when the substrate is spun, and
   each of said annular zones or sectors thereof has microchannel structures in which corresponding substructures are present at the same radial distance from the spinning axis while corresponding substructures of other zones are present at other radial distances from the spinning axis,
   wherein at least one outlet port is a waste outlet port and wherein there are no open waste outlet ports at a shorter radial distance from the spinning axis than the inlet ports.

2. The microfluidic device of claim 1, wherein said inlet ports and waste outlet ports are on different sides of the device.

3. The microfluidic device of claim 1, wherein the microchannel structures within an annular zone are divided into groups with the microchannel structures of a group being connected to each other via a common inlet microconduit or a common waste microconduit.

4. The microfluidic device of claim 1, wherein the waste outlet ports are located at the periphery of the device.

* * * * *